US011685896B2

United States Patent
Jung et al.

(10) Patent No.: US 11,685,896 B2
(45) Date of Patent: Jun. 27, 2023

(54) METHOD FOR PREPARING HIGHLY CONCENTRATED KILLED BACTERIA USING MEMBRANE FILTER AND KILLED BACTERIA PREPARED THEREBY

(71) Applicant: LACTOMASON CO., LTD., Jinju-si (KR)

(72) Inventors: Il Seon Jung, Jinju-si (KR); Jong Bin Yun, Cheonan-si (KR); Minn Sohn, Jinju-si (KR)

(73) Assignee: LACTOMASON CO., LTD., Jinju-si (KR)

( * ) Notice: Subject to any disclaimer, the term of this patent is extended or adjusted under 35 U.S.C. 154(b) by 946 days.

(21) Appl. No.: 16/426,319

(22) Filed: May 30, 2019

(65) Prior Publication Data
US 2019/0284522 A1    Sep. 19, 2019

Related U.S. Application Data

(63) Continuation of application No. PCT/KR2017/012086, filed on Oct. 30, 2017.

(30) Foreign Application Priority Data

Nov. 30, 2016 (KR) .......................... 10-2016-0162218

(51) Int. Cl.
| | | |
|---|---|---|
| C12N 1/20 | (2006.01) | |
| C12M 1/12 | (2006.01) | |
| C12N 1/02 | (2006.01) | |
| A23K 10/16 | (2016.01) | |
| A23L 33/135 | (2016.01) | |
| C12N 1/00 | (2006.01) | |
| A23L 29/00 | (2016.01) | |

(52) U.S. Cl.
CPC ................ *C12N 1/20* (2013.01); *A23K 10/16* (2016.05); *A23L 29/065* (2016.08); *A23L 33/135* (2016.08); *C12M 25/02* (2013.01); *C12N 1/005* (2013.01); *C12N 1/02* (2013.01)

(58) Field of Classification Search
CPC ..... A23K 10/16; A23L 29/065; A23L 33/135; C12M 25/02; C12N 1/005; C12N 1/02; C12N 1/20
See application file for complete search history.

(56) References Cited

U.S. PATENT DOCUMENTS

| | | | | |
|---|---|---|---|---|
| 2008/0152615 A1* | 6/2008 | Sung | ...................... | A61K 39/39 514/44 R |
| 2009/0324563 A1* | 12/2009 | Muroyama | .......... | A61K 35/747 435/252.9 |
| 2010/0098728 A1* | 4/2010 | Fujiki | .................. | A23C 20/025 424/246.1 |
| 2012/0064606 A1* | 3/2012 | Cho | ........................ | C12M 47/10 435/253.4 |
| 2015/0344841 A1* | 12/2015 | Kan | ...................... | A23L 33/135 435/244 |

FOREIGN PATENT DOCUMENTS

| | | |
|---|---|---|
| KR | 10-20080026387 A | 3/2008 |
| KR | 10-20100088894 A | 8/2010 |
| KR | 10-20120047792 A | 5/2012 |
| KR | 10-20130143229 A | 12/2013 |
| KR | 10-20140140387 A | 12/2014 |

OTHER PUBLICATIONS

International Search Report (in English) issued in PCT/KR2017/012086, dated Feb. 5, 2018.

* cited by examiner

*Primary Examiner* — Blaine Lankford
(74) *Attorney, Agent, or Firm* — Hamre, Schumann, Mueller & Larson, P.C.

(57) ABSTRACT

The present disclosure relates to a method for preparing killed lactic acid bacteria using a bioreactor including a culture device and a membrane filter, and to killed lactic acid bacteria prepared by the preparation method.

18 Claims, 19 Drawing Sheets

*FIG. 5A(i)* *FIG. 5A(ii)*
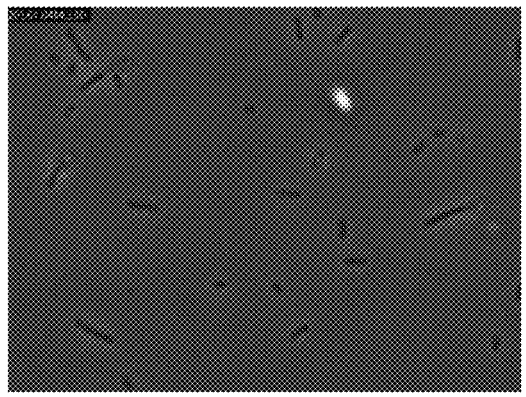 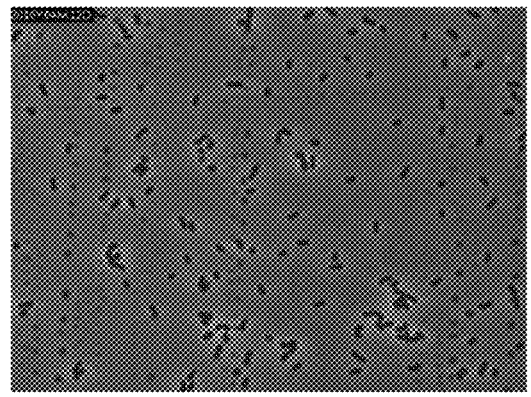
*FIG. 5A(iii)* *FIG. 5A(iv)*
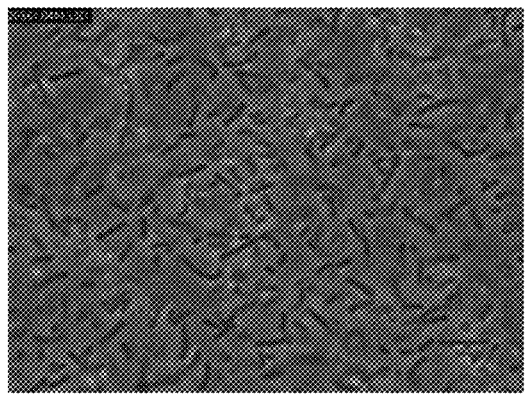 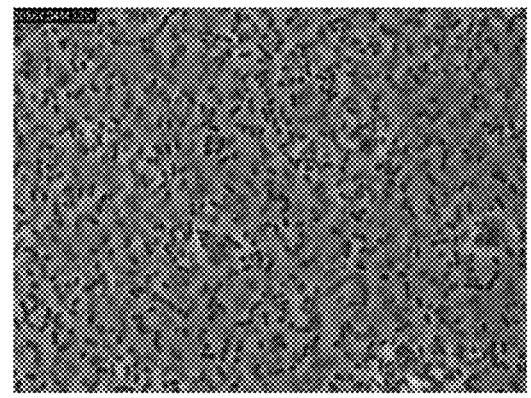
*FIG. 5B(i)* *FIG. 5B(ii)*
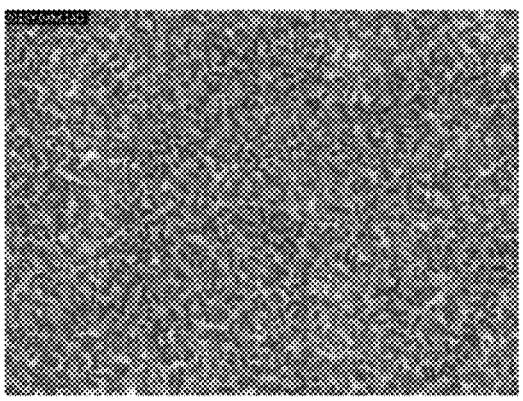 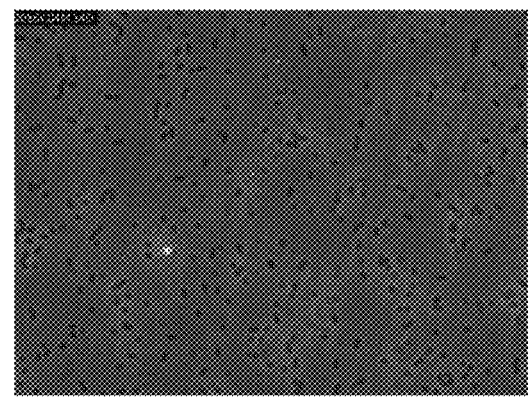

FIG. 11A(i)
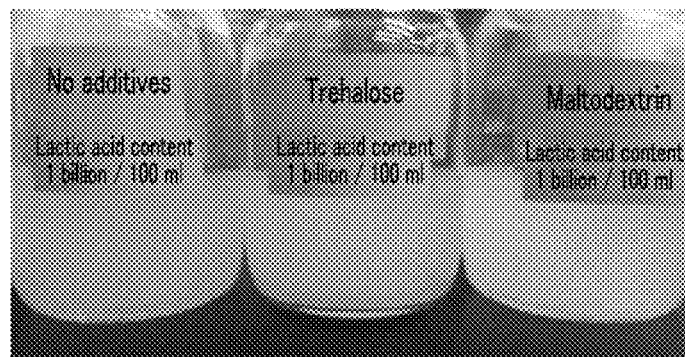
FIG. 11A(ii)
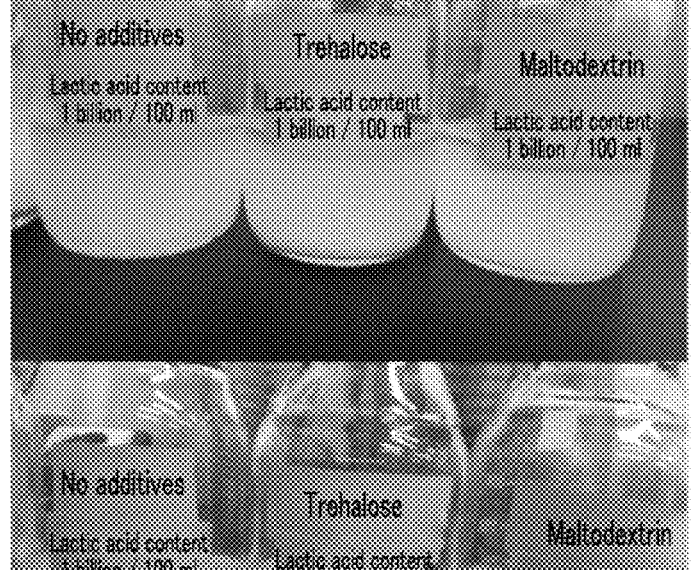
FIG. 11A(iii)
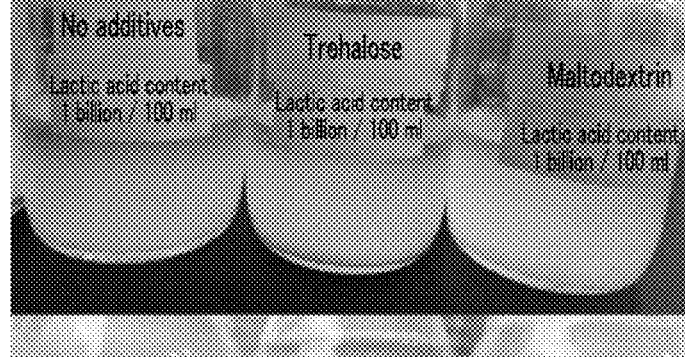
FIG. 11A(iv)
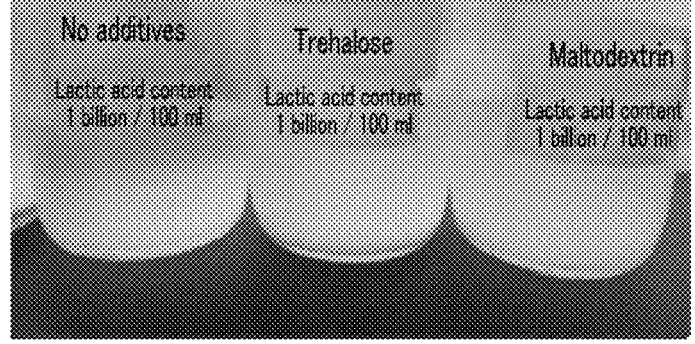

FIG. 11B(ii)

FIG. 11B(iii)

*FIG. 11C(iii)*

*FIG. 11C(iv)*

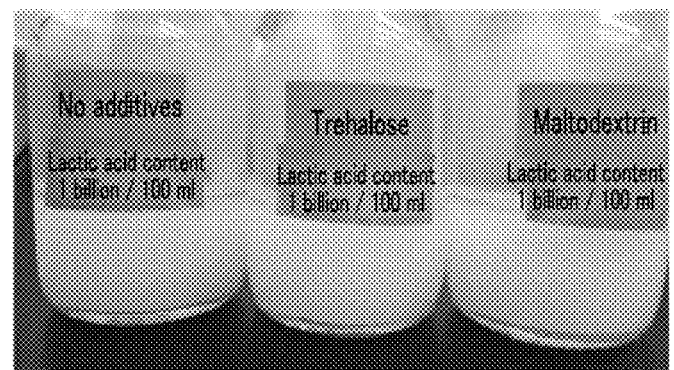
*FIG. 11D(i)*
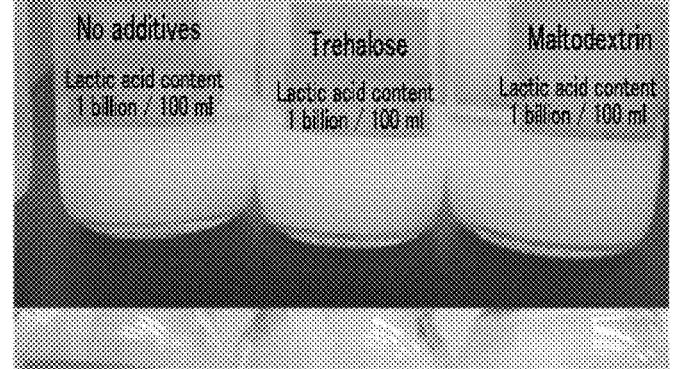
*FIG. 11D(ii)*
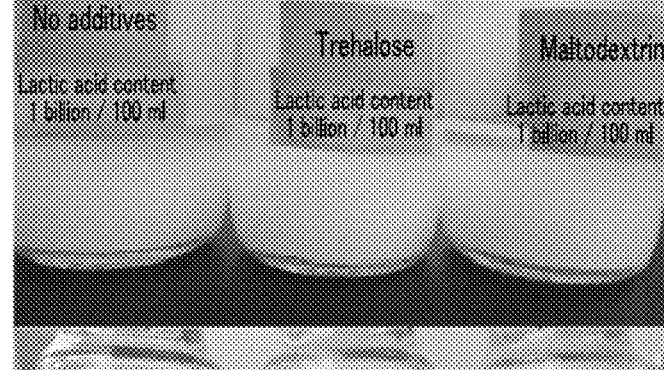
*FIG. 11D(iii)*
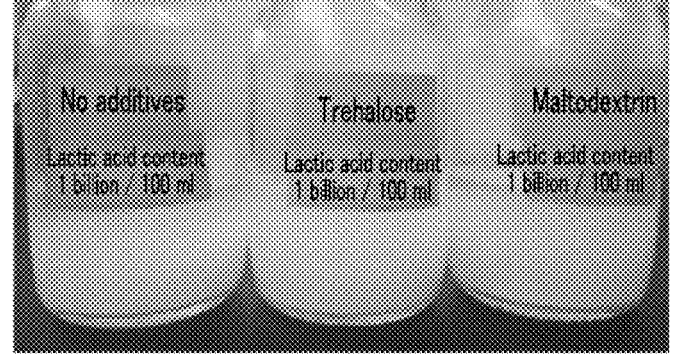
*FIG. 11D(iv)*

METHOD FOR PREPARING HIGHLY CONCENTRATED KILLED BACTERIA USING MEMBRANE FILTER AND KILLED BACTERIA PREPARED THEREBY

CROSS-REFERENCE TO RELATED APPLICATION

This application claims the benefit under 35 USC 119(a) of Korean Patent Application No. 10-2017-0162218 filed on Nov. 30, 2016 in the Korean Intellectual Property Office, the entire disclosure of which is incorporated herein by reference for all purposes.

TECHNICAL FIELD

The present disclosure relates to a method for preparing killed lactic acid bacteria using a bioreactor including a culture device and a membrane filter, and to killed bacteria prepared by the preparation method.

BACKGROUND

According to the definition by the World Health Organization (WHO), probiotics are limited to "live microorganisms that, when administered in adequate amounts, confer a health benefit on the host". However, in recent years, as the commercialization of probiotics of lactic acid bacteria has rapidly increased, killed bacteria have also been used as probiotics in the probiotics market.

Killed bacteria probiotics have various advantages over live bacteria probiotics and have already been commercialized in Japan and the U.S. The killed bacteria probiotics can be used more stably than the live bacteria probiotics and thus have broad industrial application and are easy to handle during transport. Also, the killed bacteria probiotics have been added to ordinary food to enhance the functionality of the food and have the same effect in immunoregulation as the live bacteria probiotics. Thus, in recent years, the market of killed bacteria probiotics has grown substantially.

One of conventional methods for preparing killed bacteria is a batch culture method. The batch culture method typically includes adding and culturing lactic acid bacteria with a growth medium for lactic acid bacteria in a large culture medium, and killing the cultured lactic acid bacteria by heating (Korean Patent Laid-open Publication No. 10-2012-0047792).

However, killed bacteria prepared by the batch culture method have the following disadvantages. First, the sizes of lactic acid bacteria cannot be regulated during culture of the lactic acid bacteria, and, thus, the lactic acid bacteria can grow to a size which cannot be easily absorbed in the body. Second, impurities generated during culture of lactic acid bacteria cannot be filtered rapidly, and, thus, a separate process for washing the lactic acid bacteria is needed and it takes a relatively long time to culture the lactic acid bacteria. Third, in a culture medium including lactic acid bacteria being cultured, impurities of the medium or impurities generated by the lactic acid bacteria being cultured cannot be removed selectively. Therefore, only the lactic acid bacteria cannot be selected for concentration from the culture medium including the lactic acid bacteria being cultured, and, thus, high-concentration and high-quality lactic acid bacteria cannot be prepared. The lactic acid bacteria prepared by the batch culture method agglomerate to large sizes during heat treatment. Therefore, when the lactic acid bacteria powder prepared by the batch culture method is added to food or beverage, it is deposited and causes suspension.

DISCLOSURE OF THE INVENTION

Problems to be Solved by the Invention

To solve the above-described disadvantages of the conventional method, the present disclosure provides a method for preparing killed lactic acid bacteria using a bioreactor including a culture device and a membrane filter, and killed bacteria prepared by the preparation method.

However, problems to be solved by the present disclosure are not limited to the above-described problems. Although not described herein, other problems to be solved by the present disclosure can be clearly understood by a person with ordinary skill in the art from the following description.

Means for Solving the Problems

A first aspect of the present disclosure provides a method for preparing killed lactic acid bacteria using a bioreactor including a culture device and a membrane filter. The membrane filter includes a first membrane filter and a second membrane filter and the bioreactor has a structure in which a fluid added to the culture device independently passes through the first membrane filter and the second membrane filter and then is delivered again to the culture device. The method includes: adding a medium inoculated with live lactic acid bacteria into the culture device; culturing and concentrating the live lactic acid bacteria by allowing the medium inoculated with the live lactic acid bacteria to pass through the first membrane filter; killing the cultured and concentrated live lactic acid bacteria to prepare killed lactic acid bacteria; concentrating the killed lactic acid bacteria by allowing the medium including the killed lactic acid bacteria to pass through the second membrane filter; and drying and pulverizing the concentrated killed lactic acid bacteria.

A second aspect of the present disclosure provides killed lactic acid bacteria prepared by the above-described preparation method.

A third aspect of the present disclosure provides an additive including the killed lactic acid bacteria.

Effects of the Invention

According to embodiments of the present disclosure, the first membrane filter and the second membrane filter are used to apply shear force to the live lactic acid bacteria, and, thus, it becomes easy to regulate the sizes of lactic acid bacteria. Particularly, it is possible to size down the lactic acid bacteria. Therefore, the lactic acid bacteria prepared by the preparation method of the present disclosure can be effectively absorbed into the body and can also exhibit immune activity and anti-obesity effect.

Further, according to embodiments of the present disclosure, impurities such as protein, carbohydrate, lactic acid bacteria lysate, etc. except the lactic acid bacteria can be filtered using the first membrane filter and the second membrane filter. Therefore, it is possible to provide high-concentration killed lactic acid bacteria.

Moreover, according to embodiments of the present disclosure, a process for washing lactic acid bacteria can be simplified or may not be needed. Therefore, it is possible to reduce time required for preparing live lactic acid bacteria and/or killed lactic acid bacteria.

Furthermore, according to embodiments of the present disclosure, the medium including the killed lactic acid bacteria passes through the second membrane filter to disperse agglomerated lumps of the lactic acid bacteria. Therefore, it is possible to provide high-quality killed lactic acid bacteria. When killed lactic acid bacteria powder including the high-quality lactic acid bacteria is added to food, functional food, or feed, it is not deposited and thus shows excellent transportability and storability.

BRIEF DESCRIPTION OF THE DRAWINGS

FIG. 5A shows photomicrographs (×1,000) comparing the sizes of live lactic acid bacteria cultured and concentrated according to an example of the present disclosure [FIG. 5A(ii), FIG. 5A(iv)] and live lactic acid bacteria cultured according to Comparative Example 1 [FIG. 5A(i), FIG. 5A(iii)].

FIG. 5B shows photomicrographs (×1,000) comparing the sizes of killed lactic acid bacteria prepared according to an example of the present disclosure [FIG. 5B(ii)] and killed lactic acid bacteria prepared according to Comparative Example 1 [FIG. 5B(i)].

BEST MODE FOR CARRYING OUT THE INVENTION

Figure 1:
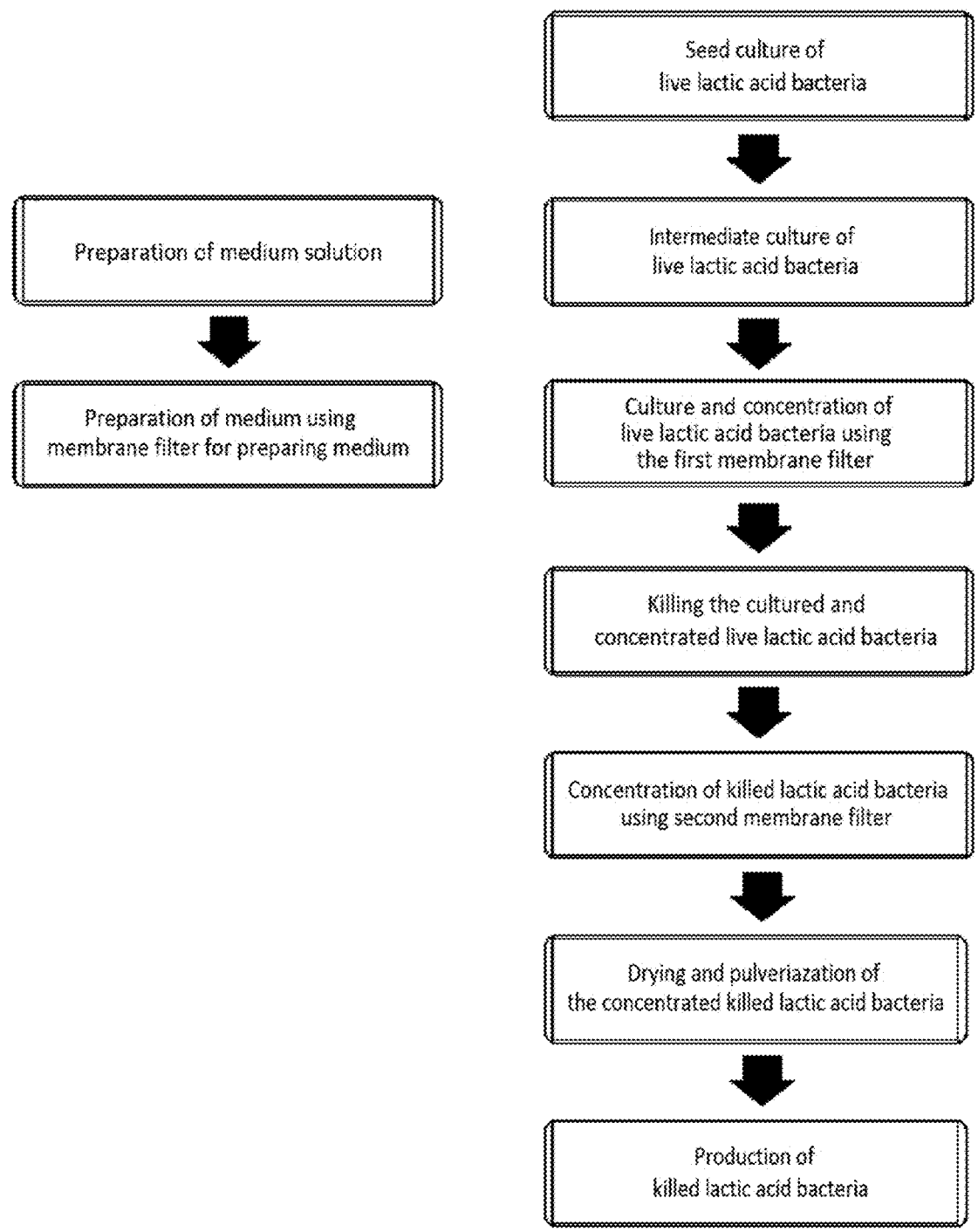
FIG. 1 is a schematic illustration of a method for preparing killed lactic acid bacteria according to an embodiment of the present disclosure.

Hereafter, examples of the present disclosure will be described in detail with reference to the accompanying drawings so that the present disclosure may be readily implemented by a person with ordinary skill in the art. However, it is to be noted that the present disclosure is not limited to the examples but can be embodied in various other ways. In the drawings, parts irrelevant to the description are omitted for the simplicity of explanation, and like reference numerals denote like parts through the whole document.

Throughout this document, the term "connected to" may be used to designate a connection or coupling of one element to another element and includes both an element being "directly connected to" another element and an element being "electronically connected to" another element via another element.

Through the whole document, the term "on" that is used to designate a position of one element with respect to another element includes both a case that the one element is adjacent to the other element and a case that any other element exists between these two elements.

Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise. Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document, the term "combination(s) of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document, a phrase in the form "A and/or B" means "A or B, or A and B".

Through the whole document, the term "bioreactor" refers to "a typical entire system that produces microorganisms such as lactic acid bacteria".

Through the whole document, the term "culture fluid" refers to "a culture medium including lactic acid bacteria" and includes "a medium inoculated with live lactic acid bacteria", "a medium including killed lactic acid bacteria", "a medium including lactic acid bacteria cultured and concentrated using a membrane filter", and "a medium including lactic acid bacteria concentrated, dispersed, and washed using a membrane filter", but is not limited thereto.

Through the whole document, the term "size of *Lactobacillus*" refers to the size of a single *Lactobacillus* or an individual *Lactobacillus*, and methods of measuring the size of *Lactobacillus* may vary depending on the kind and form of *Lactobacillus*. If the *Lactobacillus* is a *Bacillus*, the size of *Bacillus* means the length of *Bacillus* rather than the thickness or width of *Bacillus*. If the *Lactobacillus* is a *Coccus*, the size of *Coccus* means the diameter of *Coccus*. If the *Lactobacillus* is bifido *Lactobacillus* or the like, the size of bifido *Lactobacillus* refers to the size measured based on size standards generally used by a person with ordinary skill in the art.

Hereinafter, embodiments and examples of the present disclosure will be described in detail. However, the present disclosure may not be limited to the following embodiments and examples.

A first aspect of the present disclosure provides a method for preparing killed lactic acid bacteria using a bioreactor including a culture device and a membrane filter. The membrane filter includes a first membrane filter and a second membrane filter and the bioreactor has a structure in which a fluid added to the culture device independently passes through the first membrane filter and the second membrane filter and then is delivered again to the culture device. The method includes: adding a medium inoculated with live lactic acid bacteria into the culture device; culturing and concentrating the live lactic acid bacteria by allowing the medium inoculated with the live lactic acid bacteria to pass through the first membrane filter; killing the cultured and concentrated live lactic acid bacteria to prepare killed lactic acid bacteria; concentrating the killed lactic acid bacteria by allowing the medium including the killed lactic acid bacteria to pass through the second membrane filter; and drying and pulverizing the concentrated killed lactic acid bacteria.

In an embodiment of the present disclosure, the bioreactor includes the first membrane filter and the second membrane filter and thus can apply shear force to live lactic acid bacteria passing through the first membrane filter and killed lactic acid bacteria passing through the second membrane filter. In the preparation method according to an embodiment of the present disclosure, shear force is applied to the live lactic acid bacteria and the killed lactic acid bacteria, and, thus, the sizes of the lactic acid bacteria can be easily regulated. Particularly, it is possible to size down the lactic acid bacteria. Therefore, the lactic acid bacteria prepared by the preparation method according to an embodiment of the present disclosure can be effectively absorbed into the body and can also exhibit immune activity and anti-obesity effect.

Herein, the intensity of shear force applied to the fluid passing through the membrane filters can be represented by the following Equation 1 which is the Hagen-Poiseuiller equation.

$$\varphi = \frac{3\mu Q}{\pi r L^2} \qquad \text{[Equation 1]}$$

In the above Equation 1, j represents shear force on the fluid passing through a tube, m represents the viscosity of the fluid, Q represents the flow rate of the fluid, r represents the radius of the tube, and L represents the length of the tube. Further, during culture, the flow rate of the fluid may be an important factor in regulating the shear force.

Figures 2A, 2B:
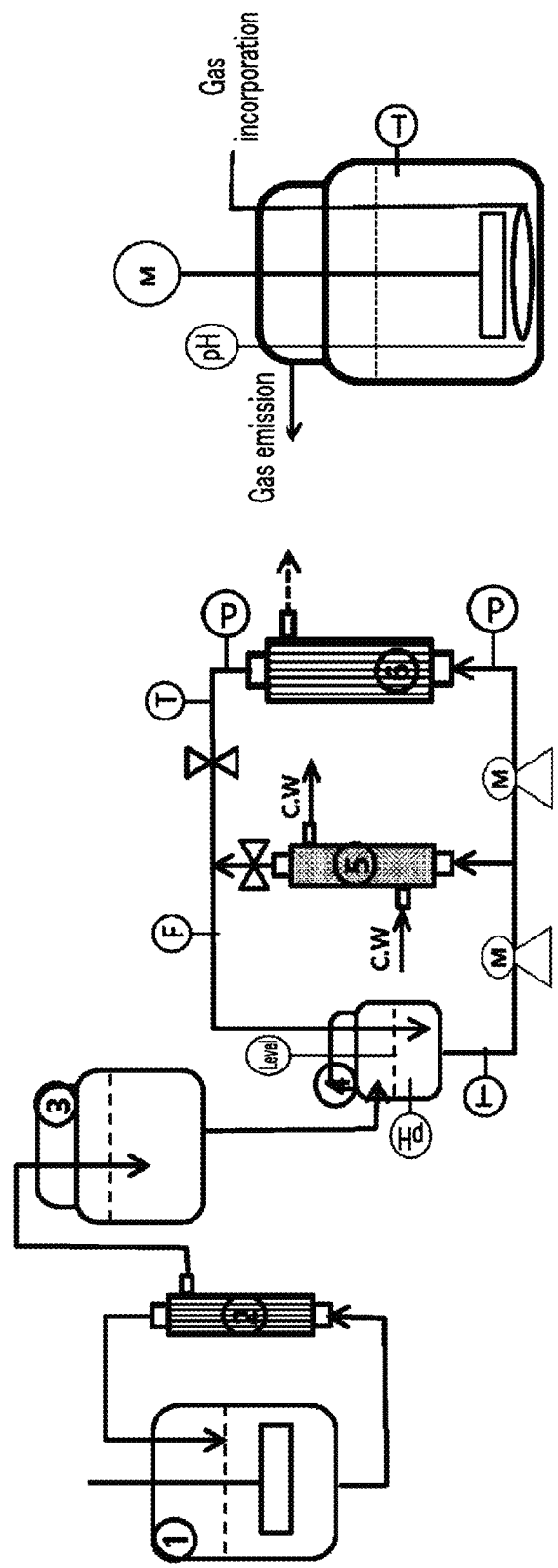
FIG. 2 is a schematic illustration comparing a bioreactor including a culture device and a membrane filter according to an embodiment of the present disclosure (FIG. 2A) and a structure of a conventional batch-type lactic acid bacteria culture device (FIG. 2B).
Figure 3A:
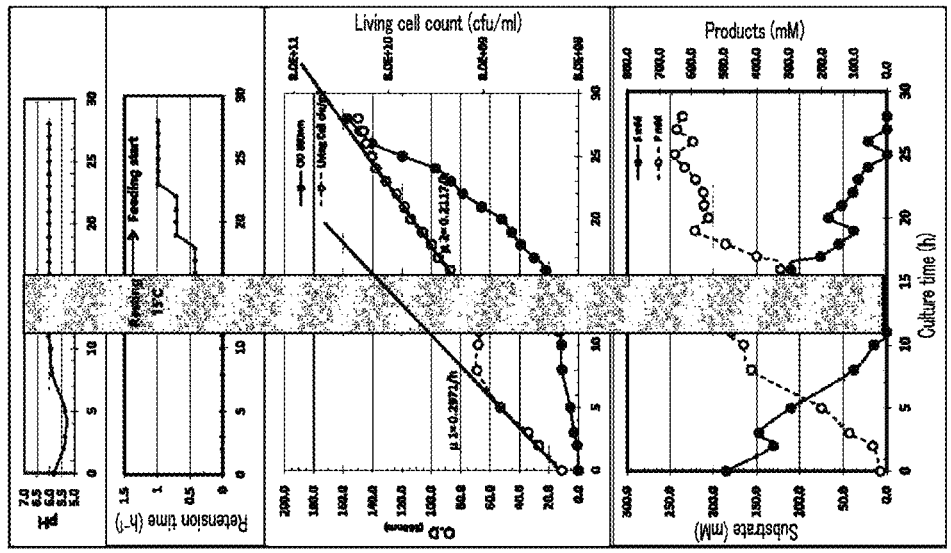
FIG. 3 shows graphs of productivity, growth rate, and concentration of live lactic acid bacteria (FIG. 3A: LM1001 and FIG. 3B: LM1004) cultured and concentrated according to an example of the present disclosure and live lactic acid bacteria cultured according to Comparative Example 1.
Figure 3B:
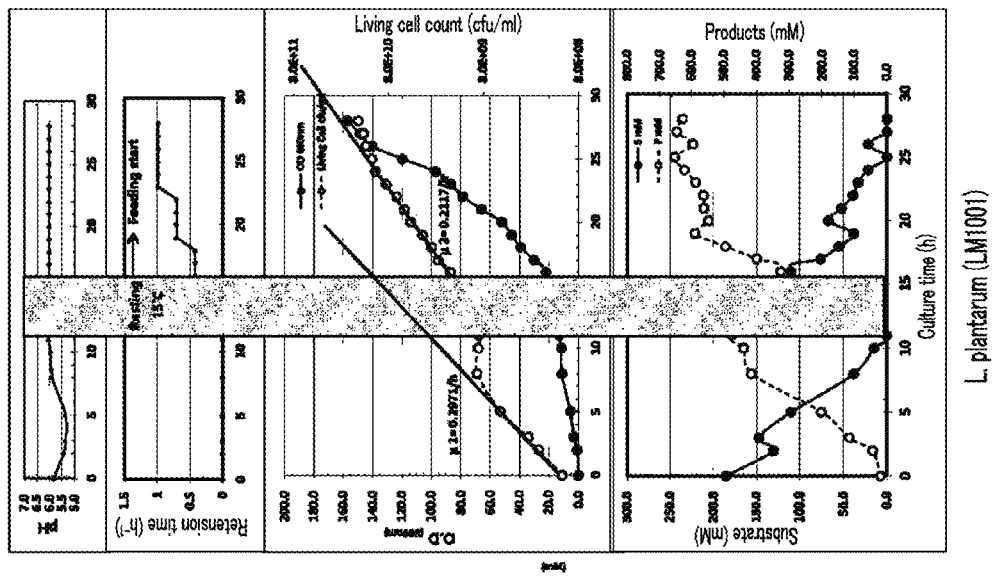

In an embodiment of the present disclosure, the bioreactor including the culture device and the membrane filter may include desirably a culture device, a first membrane filter, and a second membrane filter. Herein, the bioreactor may have a structure in which a fluid added to the culture device independently passes through the first membrane filter and the second membrane filter and then is delivered again to the culture device. FIG. 2A is a schematic illustration of a bioreactor in which a membrane filter (⑥) include both a first membrane filter and a second membrane filter. After the fluid passes through the first membrane filter and is delivered to the culture device, the fluid may pass through the second membrane filter and may be delivered to the culture device. In an embodiment of the present disclosure, the first membrane filter and the second membrane filter may be present independently of each other unlike illustrated in FIG. 2A.

The bioreactor may further include a tank for preparing a medium and a membrane filter for preparing a medium. Herein, a medium prepared in the tank for preparing a medium may pass through the membrane filter for preparing a medium and may be delivered again to the tank for preparing a medium or may be delivered to the culture device. If the medium passing through the membrane filter for preparing a medium is delivered to the culture device, the medium may pass through the membrane filter for preparing a medium and may be directly delivered to the culture device. Otherwise, as shown in FIG. 2A, the medium may be stored in a storage tank (③) before being delivered to the culture device and then may be delivered to the culture device.

The medium inoculated with the live lactic acid bacteria passes through the first membrane filter to culture and concentrate the live lactic acid bacteria. Further, a medium including killed lactic acid bacteria prepared by killing the cultured and concentrated live lactic acid bacteria passes through the second membrane filter to concentrate and disperse the killed lactic acid bacteria.

In an embodiment of the present disclosure, the first membrane filter may be a hollow fiber membrane filter including pores having a diameter large enough to filter impurities included in the medium inoculated with the live lactic acid bacteria and small enough not to filter the live lactic acid bacteria. The diameter of the pores of the first membrane filter may range, for example, from 0.1 μm to 1.0 μm, 0.2 μm to 1.0 μm, 0.3 μm to 1.0 μm, 0.4 μm to 1.0 μm, 0.5 μm to 1.0 μm, 0.1 μm to 0.9 μm, 0.1 μm to 0.8 μm, 0.1 μm to 0.7 μm, 0.1 μm to 0.6 μm, or from 0.1 μm to 0.5 μm. If the dimeter of the pores of the first membrane filter is less than 0.1 μm, fouling occurs severely during culture of the live lactic acid bacteria, and, thus, the flux of the culture fluid decreases. Therefore, the concentration efficiency of the live lactic acid bacteria may decrease. If the dimeter of the pores of the first membrane filter is more than 1.0 μm, the live lactic acid bacteria may be filtered through the membrane together with the impurities.

In an embodiment of the present disclosure, the second membrane filter may be a hollow fiber membrane filter including pores having a diameter small enough to concentrate the lactic acid bacteria whose sizes decrease during culture and concentration of the live lactic acid bacteria and/or during killing of the live lactic acid bacteria. The diameter of the pores of the second membrane filter may range, for example, from 0.01 μm to 0.1 μm, 0.02 μm to 0.1 μm, 0.03 μm to 0.1 μm, 0.04 μm to 0.1 μm, 0.05 μm to 0.1 μm, 0.01 μm to 0.09 μm, 0.01 μm to 0.08 μm, 0.01 μm to 0.07 μm, 0.01 μm to 0.06 μm, or from 0.01 μm to 0.05 μm. If the dimeter of the pores of the second membrane filter is less than 0.01 μm, fouling occurs severely during concentration of the killed lactic acid bacteria, and, thus, the flux of the culture fluid decreases. Therefore, the concentration efficiency of the killed lactic acid bacteria may decrease. If the dimeter of the pores of the second membrane filter is more than 0.1 μm, the killed lactic acid bacteria may be filtered through the membrane together with impurities.

In an embodiment of the present disclosure, each of the first membrane filter and the second membrane filter may independently include a hollow fiber membrane filter having a radius of 6.0 mm or less. If the radius of the hollow fiber membrane filter is 6.0 mm or less, the shear force applied to the live or killed lactic acid bacteria may be increased, according to Equation 1. Therefore, it is possible to size down the live or killed lactic acid bacteria and also possible to increase the dispersity.

In an embodiment of the present disclosure, the second membrane filter may include a hollow fiber membrane filter capable of filtering a material having a molecular weight of from 50,000 daltons to 100,000 daltons.

In an embodiment of the present disclosure, the bioreactor may include a pressure gauge and/or a flowmeter. Herein, the pressure gauge serves to manage fouling of the membrane filter and the flowmeter serves to measure the flow rate (Q) of the culture fluid passing through the membrane filter in real time to regulate shear force applied to lactic acid bacteria.

In an embodiment of the present disclosure, the bioreactor may further include a tank for preparing a medium and a membrane filter for preparing a medium. The medium serves to supply nutrients required for culturing live lactic acid bacteria and may be prepared by sterilizing a culture medium solution. Conventionally, a medium has been sterilized typically with steam. If the medium is sterilized with steam, carbohydrate, protein, and the like may be carbonized by heat, and, thus, impurities may be generated and may remain in the medium. Therefore, the quality of lactic acid bacteria powder may be degraded.

In an embodiment of the present disclosure, if the bioreactor includes the tank for preparing a medium and the membrane filter for preparing a medium, the membrane filter for preparing a medium may be used to filter impurities included in the culture medium solution. Thus, it is possible to suppress the generation of impurities caused by carbonization in the culture medium solution. Therefore, the preparation method according to an embodiment of the present disclosure can provide high-quality lactic acid bacteria powder. Herein, the membrane filter for preparing a medium may include a hollow fiber membrane filter having a diameter large enough to filter the impurities included in the culture medium solution. The diameter may range from 0.1 μm to 1 μm, but is not limited thereto.

In an embodiment of the present disclosure, the lactic acid bacteria may include a member selected from the group consisting of a *Bacillus*, a *Coccus*, a *Bifidobacterium*, and combinations thereof. For example, the lactic acid bacteria may include bacilli such as *Lactobacillus plantarum, L. acidophilus, L. reuteri, L. gasseri, L. crispatus, L, rhamnosus, L. casei, L. sakei, L. curvatus, L. shirota, L. reuteri, L. fermentum, L. brevis*, etc., cocci such as *Lactococcus lactis, Lactococcus lactis* subsp. *lactis, Streptococcus thermophilus, Enterococcus faecium, Enterococcus facalis*, etc., and bifidobacteria.

In an embodiment of the present disclosure, when the lactic acid bacteria includes *L. plantarum* (LM1001, Accession Number: KCCM 42959) or *L. plantarum* (LM1004, Accession Number: KCCM 43246), the effect of the present disclosure can be exhibited more remarkably.

In an embodiment of the present disclosure, the live lactic acid bacteria inoculated into the medium may be cultured through one or more culture phases. For example, the live lactic acid bacteria may be cultured through a seed culture phase and an intermediate culture phase.

In an embodiment of the present disclosure, the seed culture may be carried out desirably by inoculating live lactic acid bacteria into a liquid culture medium and culturing them at a temperature of from 20° C. to 40° C. for from 10 hours to 40 hours, but is not limited thereto. Herein, the seed culture may be carried out in anaerobic conditions depending on the kind of the lactic acid bacteria.

In an embodiment of the present disclosure, before sterilization, the pH of the liquid culture medium for the seed culture may be adjusted in the range of from pH 4.0 to pH 8.0 using a prepared alkaline solution. The composition (w/v %) of the seed culture medium may contain 2.0 w/v % to 10.0 w/v % water-containing dextrose, 0.1 w/v % to 5.0 w/v % soy protein enzyme hydrolysate, 0.1 w/v % to 5.0 w/v % casein enzyme hydrolysate, 0.1 w/v % to 5.0 w/v % yeast extract, 0.01 w/v % to 3.0 w/v % dibasic potassium phosphate, 0.1 w/v % to 5.0 w/v % magnesium sulphate, 0.01 w/v % to 1.0 w/v % calcium chloride, 0.01 w/v % to 0.1 w/v % manganese sulphate, and 0.01 w/v % to 5.0 w/v % sodium acetate, but is not limited thereto.

In an embodiment of the present disclosure, the intermediate culture serves to increase the amount of the seed cultured live lactic acid bacteria and may be carried out between the seed culture and culture and concentration of the live lactic acid bacteria using the first membrane filter. The intermediate culture may be carried out in the same conditions as the seed culture, but is not limited thereto. The intermediate culture may start by inoculating 0.1 v/v % to 5.0 v/v % of the seed culture medium into an intermediate culture medium.

In an embodiment of the present disclosure, before sterilization, the pH of the liquid culture medium for the intermediate culture may be adjusted in the range of from pH 4.0 to pH 8.0 using a prepared alkaline solution. The composition (w/v %) of the intermediate culture medium may contain 2.0 w/v % to 10.0 w/v % water-containing dextrose, 0.1 w/v % to 5.0 w/v % soy protein enzyme hydrolysate, 0.1 w/v % to 3.0 w/v % L-cysteine, 0.1 w/v % to 5.0 w/v % yeast extract, 0.01 w/v % to 3.0 w/v % dibasic potassium phosphate, 0.1 w/v % to 5.0 w/v % magnesium sulphate, 0.01 w/v % to 0.1 w/v % manganese sulphate, 0.01 w/v % to 5.0 w/v % potassium citrate, 0.01 w/v % to 2.0 w/v % calcium chloride, and 0.01 w/v % to 5.0 w/v % surfactant, but is not limited thereto.

In an embodiment of the present disclosure, after live lactic acid bacteria cultured through the one or more culture phases or live lactic acid bacteria prepared without being cultured through the one or more culture phases are inoculated into a medium, the medium inoculated with the live lactic acid bacteria is added to the culture device. Then, while the medium inoculated with the live lactic acid bacteria passes through the first membrane filter, the live lactic acid bacteria can be cultured and concentrated at the same time.

In an embodiment of the present disclosure, the medium inoculated with the live lactic acid bacteria is prepared from the culture medium solution, and the medium may be prepared by filtering impurities or contaminants included in the culture medium solution through the membrane filter followed by sterilization. Conventionally, a medium has been sterilized typically with steam. If the medium is sterilized with steam, impurities may be generated by carbonization of carbohydrate, protein, and the like and may remain in the medium. Therefore, the quality of lactic acid bacteria powder may be degraded. In an embodiment of the present disclosure, while the medium is sterilized through the medium filter, medium-derived impurities conventionally generated by steam sterilization and impurities caused by carbonization are not generated. Therefore, it is possible to provide high-quality lactic acid bacteria powder.

Herein, the medium-derived impurities may include non-aqueous protein denaturalized by heat, vitamin or nutrients destroyed by heat, and glucose decomposed or browned by heat, but are not limited thereto.

The medium inoculated with the live lactic acid bacteria only needs to grow and/or culture the live lactic acid bacteria, and may contain, for example, 1.0 w/v % to 10.0 w/v % water-containing dextrose, 0.1 w/v % to 5.0 w/v % soy protein enzyme hydrolysate, 0.1 w/v % to 5.0 w/v % yeast extract, 0.01 w/v % to 3.0 w/v % dibasic potassium phosphate, 0.1 w/v % to 5.0 w/v % magnesium sulphate, 0.01 w/v % to 0.1 w/v % manganese sulphate, and 0.01 w/v % to 2.0 w/v % calcium chloride, or may contain 0.1 w/v % to 10.0 w/v % sweet whey powder and 0.1 w/v % to 10.0 w/v % chicory extract, but is not limited thereto. The medium may further contain 0.1 w/v % to 5.0 w/v % $MgSO_4$ and 0.01 w/v % to 0.5 w/v % $CaCl_2$, but is not limited thereto.

In an embodiment of the present disclosure, the sizes of the live lactic acid bacteria may be regulated by shear force applied to the medium while the medium inoculated with the live lactic acid bacteria passes through the first membrane filter. The shear force may be regulated by the flow rate of the medium inoculated with the live lactic acid bacteria. The shear force may be controlled by the internal channel size (radius) of the hollow fiber membrane of the first membrane filter through which the medium inoculated with the live lactic acid bacteria passes and the viscosity and flow rate of the medium (see Equation 1).

According to the conventional batch-type lactic acid bacteria culture method, it is not easy to size down the lactic acid bacteria. To solve this problem, the present disclosure applies shear force to the medium including the live lactic acid bacteria to apply stress to the lactic acid bacteria being cultured, and, thus, it becomes easy to regulate the sizes of lactic acid bacteria.

The sizes of the lactic acid bacteria are known to directly affect the absorption rate of the lactic acid bacteria. Particularly, it is known that as the sizes of the lactic acid bacteria decrease, the absorption rate of the lactic acid bacteria increases and the biological effectiveness increases.

According to the preparation method of the present disclosure, as shown in Equation 1, the shear force applied to the medium can be regulated by controlling the flow rate of the medium passing through the first membrane filter. Therefore, the sizes of the live lactic acid bacteria being cultured can be regulated easily. Desirably, the sizes of the live lactic acid bacteria may be regulated to 1.0 μm or less to maximize the absorption rate. The live lactic acid bacteria regulated to relatively small sizes may be less agglomerated during a subsequent killing process and may relatively decrease in size, and, thus, the absorption of the lactic acid bacteria can be maximized.

In an embodiment of the present disclosure, the live lactic acid bacteria may be concentrated by filtering the impurities included in the medium inoculated with the live lactic acid bacteria through the first membrane filter.

In an embodiment of the present disclosure, the sizes of the live lactic acid bacteria may be regulated by allowing the live lactic acid bacteria to pass through the first membrane filter. Then, the impurities in the medium can be removed subsequently and the live lactic acid bacteria can be concentrated.

In the conventional batch-type lactic acid bacteria culture method, impurities such as protein, carbohydrate, organic acid, bacteria lysate, etc. are accumulated in the medium inoculated with the live lactic acid bacteria and attack the lactic acid bacteria and inhibit the growth of the lactic acid bacteria and thus cause a decrease in final concentration of the lactic acid bacteria.

However, according to the preparation method of the present disclosure, such impurities are filtered through the first membrane filter, and, thus, the concentration of the live or killed lactic acid bacteria can be increased. Further, since the impurities are filtered, the lactic acid bacteria can be collected through a simplified wash process. Therefore, cost reduction and process simplification can be achieved.

In an embodiment of the present disclosure, the pH of the medium inoculated with the live lactic acid bacteria may be maintained in the range of from pH 5.5 to pH 6.8 during culture of the live lactic acid bacteria. The optimum pH of the medium inoculated with the live lactic acid bacteria may vary depending on the kind of the lactic acid bacteria. In an embodiment of the present disclosure, if an organic acid produced by the lactic acid bacteria during culture lowers the pH of the medium, a material capable of maintaining a constant pH may be added into the medium. The material capable of maintaining a constant pH of the medium may include, for example, a sodium hydroxide (NaOH) solution, a potassium hydroxide (KOH) solution, an ammonia solution, or an ammonia gas, but is not limited thereto.

In an embodiment of the present disclosure, killed lactic acid bacteria may be prepared by killing the cultured and concentrated live lactic acid bacteria. The live lactic acid bacteria may be killed by, but not limited to, tyndallization or heat treatment.

In an embodiment of the present disclosure, the heat treatment may be performed at a temperature of 80° C. to 121° C. for 3 minutes to 15 minutes. Further, the heat treatment may be carried out by performing ultra-high temperature sterilization one to ten times. The ultra-high temperature sterilization may be performed at a temperature of 110° C. to 130° C. for 3.0 seconds to 10.0 seconds, for example, twice at 100° C. for 1.0 second to 10 seconds or once at 121° C. for 1.0 second to 10.0 seconds.

In an embodiment of the present disclosure, the method for preparing killed lactic acid bacteria may further include adding a dispersing agent into the medium inoculated with the live lactic acid bacteria after culture of the live lactic acid bacteria. The dispersing agent can suppress agglomeration which may occur during killing of the live lactic acid bacteria.

The dispersing agent may be added in the amount of 10.0% (w/w) to 80.0% (w/w) with respect to pellets of the cultured and concentrated live lactic acid bacteria. The dispersing agent may be maltodextrin or trehalose, but is not limited thereto.

In an embodiment of the present disclosure, the killed lactic acid bacteria may be concentrated by allowing a medium including the killed lactic acid bacteria to pass through the second membrane filter. When the medium including the killed lactic acid bacteria passes through the second membrane filter, shear force applied to the medium may be used to disperse the killed lactic acid bacteria, particularly agglomerated lumps of the killed lactic acid bacteria generated during killing of the lactic acid bacteria. Further, impurities included in the medium may be filtered, and, thus, the killed lactic acid bacteria may be washed.

In an embodiment of the present disclosure, if the medium including the killed lactic acid bacteria passes through the second membrane filter, it is possible to maximize wash and concentration of the killed lactic acid bacteria. According to this preparation method, the killed lactic acid bacteria can be concentrated desirably about ten times, nine times, eight times, seven times, six times, or five times.

The killed lactic acid bacteria are washed and then dried and pulverized. The killed lactic acid bacteria powder prepared according to the preparation method of the present disclosure may not be deposited in a solvent. According to the preparation method of the present disclosure, the live lactic acid bacteria may be regulated in size while passing through the first membrane filter. The live lactic acid bacteria with regulated sizes may agglomerate to lumps during killing of the live lactic acid bacteria, but the lumps of the killed lactic acid bacteria may be dispersed by shear force while passing through the second membrane filter. Therefore, even when the dispersed killed lactic acid bacteria are pulverized, agglomeration of the killed lactic acid bacteria does not occur. Accordingly, it is possible to suppress deposition of the killed lactic acid bacteria powder in the solvent.

In an embodiment of the present disclosure, the lactic acid bacteria culture fluid may be washed to filter impurities such as protein, carbohydrate, lactic acid bacteria lysate, etc. except the lactic acid bacteria.

In an embodiment of the present disclosure, a wash solution may be added to the culture device and then, the killed lactic acid bacteria may be allowed to pass through the second membrane filter to maximize the washing effect of the lactic acid bacteria with the second membrane filter. Herein, the wash solution may include, for example, sterilized distilled water and distilled water containing 0.1 w/v % to 1.0 w/v % sodium chloride (NaCl), but is not limited thereto. The volume of the wash solution to be added may be from 1.0 time to 10 times the volume of the medium including the concentrated killed lactic acid bacteria.

In an embodiment of the present disclosure, the drying may be lyophilization, fluid-bed drying, or spray drying, but is not limited thereto.

In an example of the present disclosure, the pulverized killed lactic acid bacteria may have sizes ranging from 0.01 μm to 3.0 μm, from 0.1 μm to 3.0 μm, or from 0.5 μm to 3.0 μm. Herein, 40% to 100% of the pulverized killed lactic acid bacteria may have sizes of 1.0 μm or less.

A second aspect of the present disclosure provides killed lactic acid bacteria prepared by the above-described preparation method.

A third aspect of the present disclosure provides an additive including the killed lactic acid bacteria.

In an embodiment of the present disclosure, the additive may be added to food, functional food, or feed, but is not limited thereto.

The killed lactic acid bacteria powder prepared by the preparation method of the present disclosure has small particle sizes with uniform dispersion and distribution of killed lactic acid bacteria. Further, the killed lactic acid bacteria powder is obtained through filtering of impurities with the first membrane filter and the second membrane filter, and, thus, a relatively small amount of impurities may remain. Therefore, the preparation method of the present disclosure can provide high-quality killed lactic acid bacteria powder.

When the high-quality killed lactic acid bacteria powder is added to food, functional food, or feed, it is not deposited and thus shows excellent transportability and storability.

MODE FOR CARRYING OUT THE INVENTION

Hereafter, examples of the present disclosure will be described in detail. However, the present disclosure may not be limited thereto.

EXAMPLES

1. Origin of Lactic Acid Bacteria

*L. plantarum* (LM1001) and *L. plantarum* (LM1004) used herein were isolated from kimchi, Korean traditional fermented food, obtained from Department of Pharmaceutical Engineering of International University of Korea [Address: 965, Dongbu-ro, Munsan-eup, Jinju-si, Gyeongsangnam-do 660-759, Republic of Korea]. *L. plantarum* (LM1001) and *L. plantarum* (LM1004) were deposited in the Korean Culture Center of Microorganisms (KCCM)'s general collection and named KCCM 42959 (Date of deposit: Nov. 12, 2010) and KCCM 43246 (Date of deposit: Oct. 28, 2016), respectively.

All the lactic acid bacteria used in Examples or Test Examples described below *L. plantarum* (LM1001) and *L. plantarum* (LM1004) unless otherwise stated.

2. Analysis Method 2-1. Viable Cell Count Analysis

The viable cell count of the lactic acid bacteria increased during culture was analyzed by colony counting. In this case, to analyze colonies of *L. plantarum*, solid MRS medium (Difco, USA) was used, culture was carried out at 37° C. for 48 hours in anaerobic conditions, and the number of colonies produced was measured. A culture device was JRS-150C.

A culture fluid was diluted at a rate of $10^7$, $10^8$, or $10^9$ using peptone water and then poured in the amount of 1.0 ml per Petri-dish.

The composition (w/v %) of the peptone water used for dilution of the culture fluid was as follows: 0.01 w/v % to 1.0 w/v % sodium chloride, 0.1 w/v % to 5.0 w/v % casein enzyme hydrolysate, 0.01 w/v % to 5.0 w/v % dibasic sodium phosphate, and 0.01 w/v % to 1.0 w/v % monobasic potassium phosphate. The peptone water was used after sterilization (at 121° C. for 15 minutes).

2-2. Total Cell Count Analysis

After the culture fluid was sterilized, the number of killed lactic acid bacteria in the culture fluid was analyzed using a hemocytometer. The number of killed bacteria in a total of 20 rooms of the hemocytometer was measured using a ×1000 optical microscope (BX 53F, Olympus, Japan) and the average $N_{avg}$ was obtained. Then, the total cell count (No/g or ml of powder) was analyzed using the following Equation 2.

$$N_O=(N_{avg})(4)(10^6)(R) \qquad \text{Equation 2}$$

Herein, R represents dilution rate.

To analyze the total cell count in the killed lactic acid bacteria powder, 1.0 g of dry powder was dissolved in 10 ml of distilled water and well suspended and then diluted in sterilized distilled water at a rate of $10^8$, $10^9$, or $10^{10}$.

2-3. HPLC Analysis of Glucose and Lactic Acid

During culture, an HPLC (Agilent Technology 1200, Agilent, USA) was used for analyzing glucose and organic acid such as lactic acid. An amine column ($NH_2$, 300 mm×7.8 mm, 9.0 mm particle size, Bio-Rad, USA) and a 5 mM $H_2SO_4$ solution (0.5 ml flow rate) were used for stationery phase and mobile phase, respectively. During analysis, the temperature of the column was maintained at 35° C. and the sample was automatically injected with an autosampler (5.0 mL). The analysis was conducted using an Agilent Chemstation 1200 with an R.I detector.

2-4. Immune Activity Analysis Method

The immune activity and cytotoxicity of heat-killed probiotics (HK-probiotics) were evaluated by analyzing changes in production of interleukin-12 (IL-12), interleukin-4 (IL-4), interferon-gamma (INF-$\gamma$), TNF-alpha (TNF-$\alpha$), and NO (nitric oxide) and the viability and proliferation of immune cells in in-vitro analysis using macrophages (RAW 264.7) and splenocytes in a mouse spleen.

2-4-1. Preparation of Samples

Live lactic acid bacteria and killed lactic acid bacteria samples were prepared by the preparation method of the present disclosure using *L. plantarum* (LM1001).

The live lactic acid bacteria sample was analyzed through an in-vivo test in which diluted live lactic acid bacteria were orally administered to mice at a certain concentration and changes in cytokines in blood of the mice were measured, and the immune activity of the killed lactic acid bacteria was analyzed through an in-vitro test in which the killed lactic acid bacteria were treated for each concentration using mouse splenocytes and macrophages (RAW 264.7) and changes in cytokines were measured.

2-4-2. Test Animals and Treatment 6-week-old male Balb/c mice were purchased from Samtako Inc. (Korea). They were raised at a temperature of 22±2° C. and a humidity of 50±20% and exposed to light for 12 hours and freely fed with solid feed for mouse and tap water as drinking water. After an adaptation period of 1 week, the test was conducted to the animals.

The live lactic acid bacteria of *L. plantarum* (LM1001) prepared according to the preparation method of the present disclosure were orally administered to the mice once a day for 10 days. Blood samples were obtained from the test animals 24 hours after the last oral administration and kept at −80° C. and used for the test. A positive control was administered intravenously with 25 mg/kg of Con A.

2-4-3. Isolation and Culture of Mouse Splenocytes

The spleen was aseptically extracted from the mice and washed with an RPMI 1640 solution and then crushed to isolate cells. An isolated cell suspension was allowed to pass through a 200-mesh stainless steel sieve and centrifuged at 4° C. and 1,200 rpm for 3 minutes and cell pellets were suspended in an ACK buffer for 5 minutes to remove red blood cells. The extracted splenocytes were suspended in the RPMI 1640 containing 10% fetal bovine serum and 1% penicillin-streptomycin to a concentration of $1\times10^6$ cell/ml and seeded 500 µl per well into a 48-well plate and treated with the killed lactic acid bacteria of *L. plantarum* prepared according to the preparation method of the present disclosure for each concentration. Positive controls were treated with lipopolysaccharides and Con A, respectively.

The cell groups treated as described above were cultured at 37° C. and 5% $CO_2$ in an incubator for from 3 hours to 73 hours, and a supernatant of the culture fluid was kept at −20° C. and used for measuring the amount of cytokine produced.

2-4-4. Cell Culture

The splenocytes and RAW 264.7 cells were cultured using a DMEM medium containing 10% fetal bovine serum and 100 units/ml of streptomycin and penicillin at 37° C. and 5% $CO_2$ and used to find out the effect on NO and cell proliferation rate.

2-4-5. Measurement of Cytokine (IFN-$\gamma$, TNF-$\alpha$, IL-12) Secretion Ability After the splenocytes were cultured, the amounts of cytokines (TNF-$\alpha$, IFN-$\gamma$, IL-12) secreted from the culture supernatant were measured. The killed lactic acid bacteria samples of *L. plantarum* (LM1001) prepared according to the preparation method of the present disclosure were treated together with the positive controls LPS and Con A for a certain period of time, and then, the concentrations of cytokines isolated in the culture fluid were measured by enzyme linked immmuosorbent assay (ELISA) (ELISA kit, R&D system, USA).

That is, 100 µl of the supernatant sample was placed in a 96-well plate coated with an antibody to cytokines and reacted at room temperature for 2 hours and the supernatant solution was removed, followed by washing three or more times with a wash solution prepared by mixing phosphate buffered saline and Tween-20 (Sigma).

Then, a solution containing a secondary antibody was placed to react with the primary antibody, and then horseradish peroxidase (HRP) conjugated with avidin was added thereto and reacted at room temperature for 15 minutes.

Then, a TMB solution was added as a substrate for the HRP and reacted. Then, changes in color were checked.

The color changed depending on the concentrations of cytokines present in the sample. Therefore, whether or not cytokines were produced in the sample could be found based on the color changes. After the reaction between the HRP and the TMB substrate was terminated by adding sulfuric acid (1.0 M), the absorbance at 450 nm was measured using a microplate reader (Thermo).

2-4-6. Measurement of NO

The macrophages RAW 264.7 were seeded at a concentration of $5 \times 10^5$ cells/ml into a 96-well plate and cultured for 24 hours. Then, a positive control was treated with 1 mg/ml of LPS and a negative control was treated with phosphate buffered saline. The killed lactic acid bacteria samples of *L. plantarum* (LM1001) were treated and then cultured again for 24 hours.

The concentration of NO was measured using a Griess reagent system (Sigma, USA). 50 μl of the culture fluid was added to a 96-well plate and Griess reagent I (NED solution) and Griess reagent II (sulfaniliamide solution) were added and mixed in the same amount. After reaction for 10 minutes in a darkroom, the absorbance at 540 nm was measured within 30 minutes using a microplate reader (Tecan, Austria). The concentration of NO was calculated using a standard curve (0~100 μM) of sodium nitrite.

2-4-7. Measurement of Cell Proliferation Rate

The cell proliferation rates of the splenocytes and macrophages RAW 264.7 were measured by WST-1 analysis. The splenocytes and macrophages RAW 264.7 were seeded at a concentration of $5 \times 10^5$ cells/well into a 96-well plate, and the samples and controls were treated and cultured for 48 hours. After addition of 100 μl of a WST-1 kit solution and culture for 1 hour, the absorbance at 540 nm was measured using an ELISA reader (Thermo, Germany) and represented by the following Equation 3.

$$N(\%) = \left[\frac{C_p}{C_s}\right] 100 \quad \text{[Equation 3]}$$

Herein, N (%) represents cell proliferation rate, $C_p$ represents absorbance after killing treatment, and $C_s$ represents absorbance without treatment.

2-4-8. Statistical Analysis

The results were analyzed using the SPSS 21 manual (Statistical Package for Social Sciences, IBM, Armonk, N.Y., USA) through one way ANOVA test, and statistical significances of the samples were compared by using Student two-tailed t test with $P<0.05$.

2-5. Anti-Obesity Effect of Lactic Acid Bacteria

The killed lactic acid bacteria samples prepared according to the embodiment were treated for each concentration while differentiation of preadipocytes (3T3-L1 cells) to mature adipocytes was induced. Then, Oil Red-O staining was performed to check the effect of inhibiting lipid accumulation in the adipocytes and the content of triglycerides in cells (TG kit) was measured to check the degree of lipid accumulation in cells.

2-5-1. Preadipocyte Growth Inhibition Effect

To analyze the anti-obesity effect of lactic acid bacteria, MTT (methylthiazolinyldiphenyl tetrazolium bromide) assay was performed on a preadipocyte 3T3-L1 (Mouse Embryonic Fibroblast-Adipose like cell line) culture fluid to analyze the cytotoxicity of the killed lactic acid bacteria.

The preadipocytes 3T3-L1 were seeded at $4 \times 10^4$ cells/ml in a 96-well plate and cultured for 24 hours at 5% $CO_2$ and 37° C. in an incubator. After culture, the culture fluid was removed and the DMEM medium and the killed lactic acid bacteria powder were treated for respective concentrations (0 μg/ml, 100 μg/ml, 250 μg/ml, and 500 μg/ml) for 24 hours. Then, an MTT (3-[4,5-dimethyl-thiazol]-2,5-diphenyl-tetrazolium bromide) solution dissolved 5 mg/ml in a solvent DPBS (Dulbecco's Phosphate-Buffered Saline, 1×) was seeded 120 μl per well and cultured for 4 hours at 5% $CO_2$ and 37° C. in an incubator.

After culture, the culture fluid was removed, and 200 μl of dimethyl sulfoxide (DMSO) was added to each well and stirred well using a pipette. Then, the absorbance at 570 nm was measured using the ELISA reader.

2-5-2. Measurement of Lipid Accumulation Inhibition Activity in Adipocytes (Oil Red-O Staining Analysis)

The preadipocytes 3T3-L1 were seeded at a density of $7 \times 10^4$ cells/ml into a 6-well plate and differentiated for 8 days at the same time when the killed lactic acid bacteria powder were treated for respective concentrations (100 μg/ml, 250 μg/ml, and 500 μg/ml). After 8 days, the cell culture fluid was removed, followed by wash with phosphate buffered saline (PBS). Then, 10% formaldehyde was placed 500 μl per well and immobilized at 4° C. for 1 hour, after removal of formaldehyde, the plate was washed three times with PBS and then dried in a $CO_2$ incubator.

After the plate was completely dried, Oil Red-O stain was added 500 μl per well and left for staining at room temperature in the dark for 30 minutes and then washed three times with PBS. The stained cells were examined under a microscope. After examination, 300 μl of iso-propanol per well was used to extract the stain in the adipocytes. Then, an optical density value (OD value) at 500 nm was measured using the ELISA reader.

The Oil Red-O stain was used after a solution in which 500 mg of the Oil Red-O stain was dissolved in 100 ml of iso-propanol was mixed with distilled water at a ratio of 6:4 and then filtered with a 0.45 μm filter.

2-5-3. Analysis of Content of Triglycerides in Adipocytes

The preadipocytes 3T3-L1 were seeded at a density of $7 \times 10^4$ cells/ml into a 6-well plate and differentiated for 8 days at the same time when the killed lactic acid bacteria powder were treated for respective concentrations (100 μg/ml, 250 μg/ml, and 500 μg/ml).

After 8 days, each well was washed with PBS. Then, cells were collected using a cell scraper (SPL) and triglycerides in the cells were extracted using an ultrasonicator (SONIFIER 450, BRANSON) and the content of the triglycerides was measured using a triglyceride kit (TG-S, ASAN Pharm. Co., Ltd.).

Example 1. Culture and Concentration of Live Lactic Acid Bacteria 1-1. Storage of Live Lactic Acid Bacteria Lactic acid bacteria used in Examples of the present disclosure were cultured at 37° C. using solid MRS (Difco. USA) for 48 hours in anaerobic conditions. After 48 hours, *Lactobacillus* colonies appearing on the medium were harvested in an aseptic bench and washed three times with phosphate buffered saline (PBS, pH 6.8). Then, an appropriate cryoprotectant (25% glycerin+10% skimmed milk powder) was added and suspended and then seeded 0.2 ml into each Cryo-vial (1.2 ml, Simport, Canada) prior to freezing at −70° C. in a cryogenic freezer.

The defreezed vials (DF vials) were kept for up to six months and melted for use whenever needed. All the tests were carried out in aseptic conditions to minimize contamination.

1-2. Seed Culture of Live Lactic Acid Bacteria

After the vials were taken out of the cryogenic freezer and melted, seed culture of live lactic acid bacteria was conducted.

Firstly, the DF vials (0.2 ml) were inoculated into 15 ml of sterilized liquid MRS medium (Difco, USA) (18f, test tube) and cultured at 37° C. for 12 hours in a culture device (JSBI-150C, JSR Korea) in anaerobic conditions.

Secondly, 15 ml of liquid lactic acid bacteria cultured for 12 hours was inoculated into 1.0 L of seed culture medium LTMS-PR-SM (four 2.0 L-conical flasks) and cultured at 37° C. for 10 hours in a culture device (JSBI-150C, JSR Korea) in anaerobic conditions.

The composition (w/v %) of the seed culture medium LTMS-PR-SM was as follows: 2.0 w/v % to 10.0 w/v % water-containing dextrose, 0.1 w/v % to 5.0 w/v % soy protein enzyme hydrolysate, 0.1 w/v % to 5.0 w/v % casein enzyme hydrolysate, 0.1 w/v % to 5.0 w/v % yeast extract, 0.01 w/v % to 3.0 w/v % dibasic potassium phosphate, 0.1 w/v % to 5.0 w/v % magnesium sulphate, 0.01 w/v % to 1.0 w/v % calcium chloride, 0.01 w/v % to 0.1 w/v % manganese sulphate, and 0.01 w/v % to 5.0 w/v % sodium acetate, and the pH of the seed culture medium LTMS-PR-SM was adjusted to pH 6.8 using NaOH (10.0 M) before sterilization.

1-3. Intermediate Culture of Live Lactic Acid Bacteria 1.5 L of the seed culture fluid cultured during seed culture was used to be inoculated into 80 L of intermediate culture medium LTMS-PR-MM (100 L-fermentor, KoBioTech). The intermediate culture was carried out at 32° C. for 12 hours with slight stirring. An ammonia gas was regularly added to adjust the pH of the culture fluid in the range of from pH 5.0 to pH 7.0 whenever needed.

The composition (w/v %) of the intermediate culture medium was as follows: 2.0 w/v % to 10.0 w/v % water-containing dextrose, 0.1 w/v % to 5.0 w/v % soy protein enzyme hydrolysate, 0.1 w/v % to 3.0 w/v % L-cysteine, 0.1 w/v % to 5.0 w/v % yeast extract, 0.01 w/v % to 3.0 w/v % dibasic potassium phosphate, 0.1 w/v % to 5.0 w/v % magnesium sulphate, 0.01 w/v % to 0.1 w/v % manganese sulphate, 0.01 w/v % to 5.0 w/v % potassium citrate, 0.01 w/v % to 2.0 w/v % calcium chloride, and 0.01 w/v % to 5.0 w/v % Tween-80, the pH of the intermediate culture medium was adjusted to pH 6.8 using NaOH (10.0 M) before sterilization.

1-4. Culture and Concentration of Live Lactic Acid Bacteria Using First Membrane Filter A bioreactor used in the preparation method of the present disclosure includes a first membrane filter (a hollow fiber membrane filter including pores having a diameter of 0.5 μm and having a channel radius of 6 mm, an Al—Al ceramic hollow fiber membrane filter) and a culture device. The membrane filter is located outside the culture device, and a culture fluid is inoculated into the culture device and then the membrane filter and the culture device are circulated using a forced aseptic circulating pump (Q=9.0 m³/h, $H_{max}$=41 m, 5.0 bar, 120° C.).

First, 20 L of a medium inoculated with the live lactic acid bacteria cultured through the seed culture and the intermediate culture was inoculated into the culture device. Then, the medium including the live lactic acid bacteria was allowed to pass through the first membrane filter using the forced aseptic circulating pump. Thus, the live lactic acid bacteria were cultured while being concentrated and filtered.

Through the concentration and filtering processes, the intermediate culture medium was filtered and a new medium was also added to the culture device. The composition (w/v %) of the newly inoculated medium was as follows: 2.0 w/v % to 10.0 w/v % water-containing dextrose, 0.1 w/v % to 5.0 w/v % soy protein enzyme hydrolysate, 0.1 w/v % to 5.0 w/v % yeast extract, 0.01 w/v % to 3.0 w/v % dibasic potassium phosphate, 0.1 w/v % to 5.0 w/v % magnesium sulphate, 0.01 w/v % to 0.1 w/v % manganese sulphate, and 0.01 w/v % to 2.0 w/v % calcium chloride. The newly inoculated medium was previously sterilized through a medium filter (an Al—Al ceramic hollow fiber membrane filter including pores having a dimeter of 0.2 μm and having a channel radius of 6 mm) before being added to the culture device.

After the intermediate culture medium was entirely replaced with the newly added medium, the culture device was cooled to 18° C. or less and the flow of the culture fluid flowing through the first membrane filter was maintained to a minimum. The pH of the medium was maintained in the range of from 5.0 to 6.8 (1:1=20 w/v % ammonia solution: distilled water) for 5 hours until culture and concentration of the live lactic acid bacteria started.

Then, the temperature of the bioreactor was increased to 32° C. before culture and concentration of the live lactic acid bacteria started, and a culture fluid including the medium inoculated with the live lactic acid bacteria was allowed to pass through the first membrane filter. As such, substantive culture for culturing and concentrating the live lactic acid bacteria started. When the culture fluid passed through the first membrane filter, the volume of the culture fluid decreased at a constant rate. Thus, the newly inoculated medium was continuously supplied to the culture device in aseptic conditions using a pump (YZ15, Leadfluid, China, Max=20.0 L/h).

Then, the flow rate of the medium circulating through the first membrane filter was adjusted to 50.0 L/h to 300.0 L/h by using the forced aseptic circulating pump, and the inside of the bioreactor was maintained at a pH of from 5.0 to 7.0 using ammonia solution (1:1=20 w/v % ammonia solution: distilled water). An internal pressure of a fermentor was maintained in the range of from 0.1 kg/cm² to 0.5 kg/cm² using a nitrogen gas to maintain the anaerobic conditions.

Example 2. Killing of Live Lactic Acid Bacteria

In an example of the present disclosure, prior to killing of the live lactic acid bacteria obtained from Example 1, Group 1 in which a dispersing agent was not added to the medium inoculated with the live lactic acid bacteria and Groups 2 and 3 in which 0.1 wt % to 80.0 wt % maltodextrin and 0.1 wt % to 80.0 wt % trehalose were added as a dispersing agent to the respective media were prepared.

In an example of the present disclosure, the live lactic acid bacteria obtained from Example 1 were circulated three times at 121° C. for 3 seconds by using a ultra-high temperature continuous sterilizer to prepare killed lactic acid bacteria (Example 2-1).

In an example of the present disclosure, the live lactic acid bacteria obtained from Example 1 were circulated at 110° C. for five seconds by using a ultra-high temperature continuous sterilizer to prepare killed lactic acid bacteria (Example 2-2, FIG. 5B).

Figure 7:
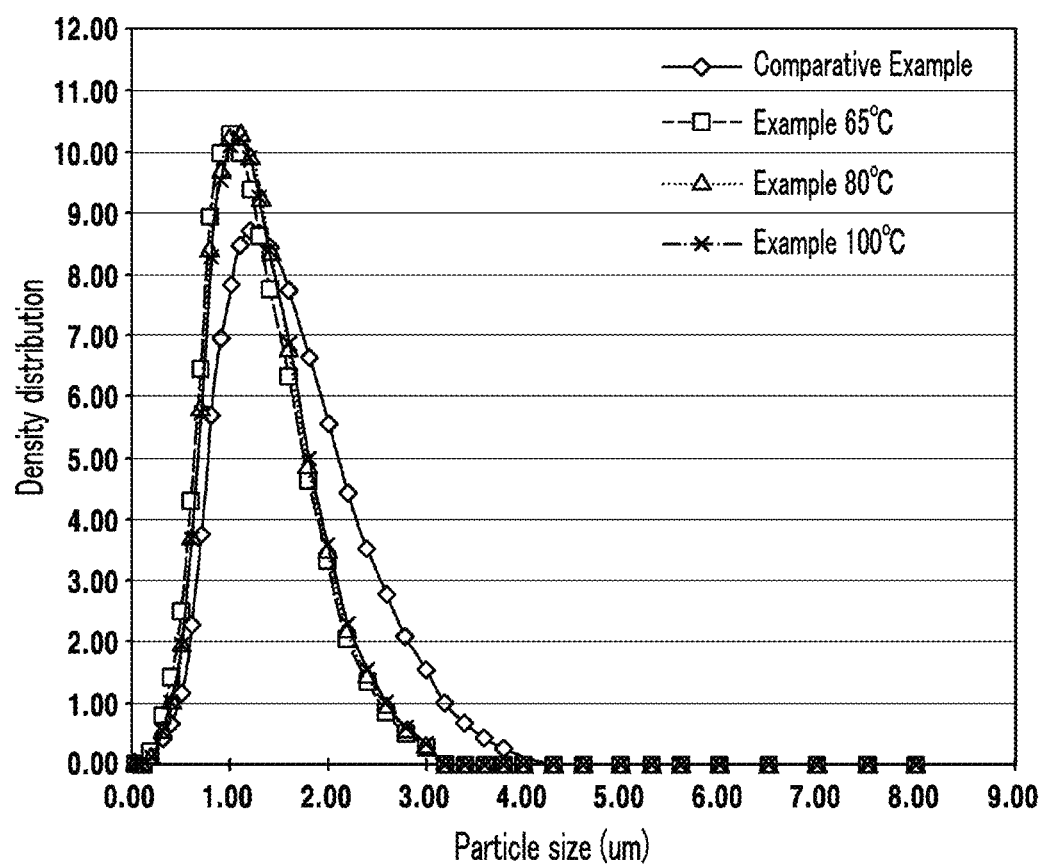
FIG. 7 is a graph comparing size distributions of killed lactic acid bacteria prepared according to an example of the present disclosure and killed lactic acid bacteria prepared according to Comparative Example 1.
Figure 8A:
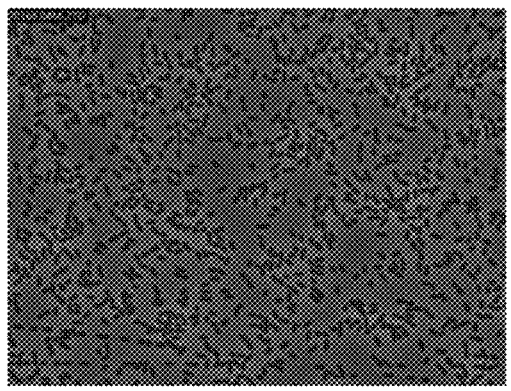
FIG. 8 shows photomicrographs (×1,000) showing the sizes of live lactic acid bacteria (FIG. 8A, FIG. 8C and FIG. 8E: LM1001, FIG. 8B, FIG. 8D and FIG. 8F: LM1004) right after culture and concentration (FIG. 8A, FIG. 8B), right after killing (FIG. 8C, FIG. 8D), and right after concentration and wash (FIG. 8E, FIG. 8F) in a preparation method according to an example of the present disclosure.
Figure 8B:
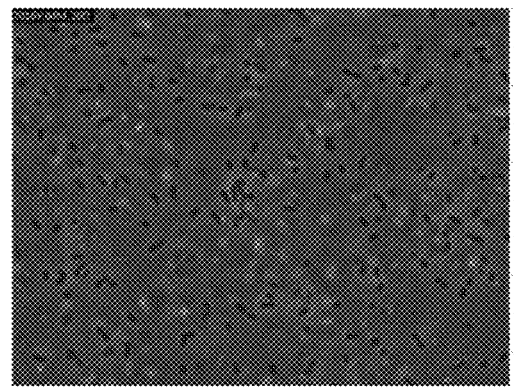
Figure 8C:
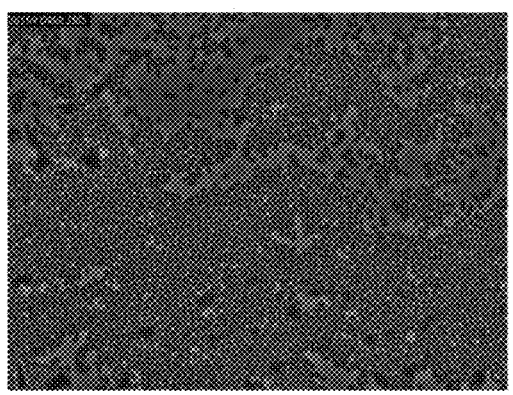
Figure 8D:
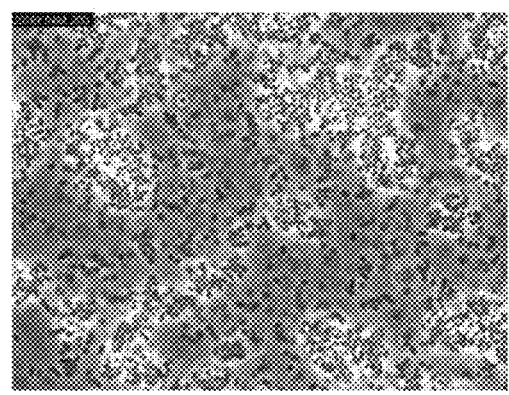
Figure 8E:
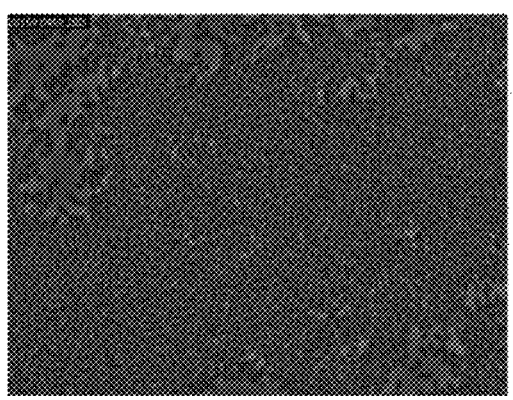
Figure 8F:
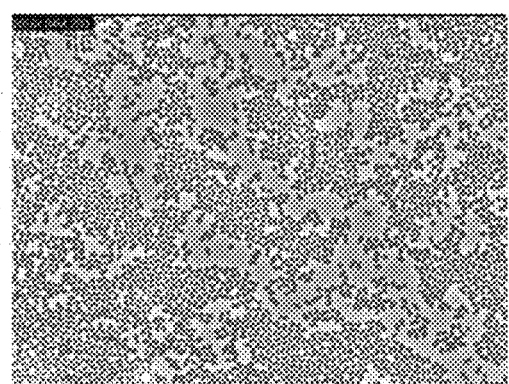

In an example of the present disclosure, the live lactic acid bacteria obtained from Example 1 were circulated at 65° C., 85° C., and 120° C., respectively, for three seconds by using a ultra-high temperature continuous sterilizer to prepare killed lactic acid bacteria (Example 2-3, FIG. 7).

Figure 9A:
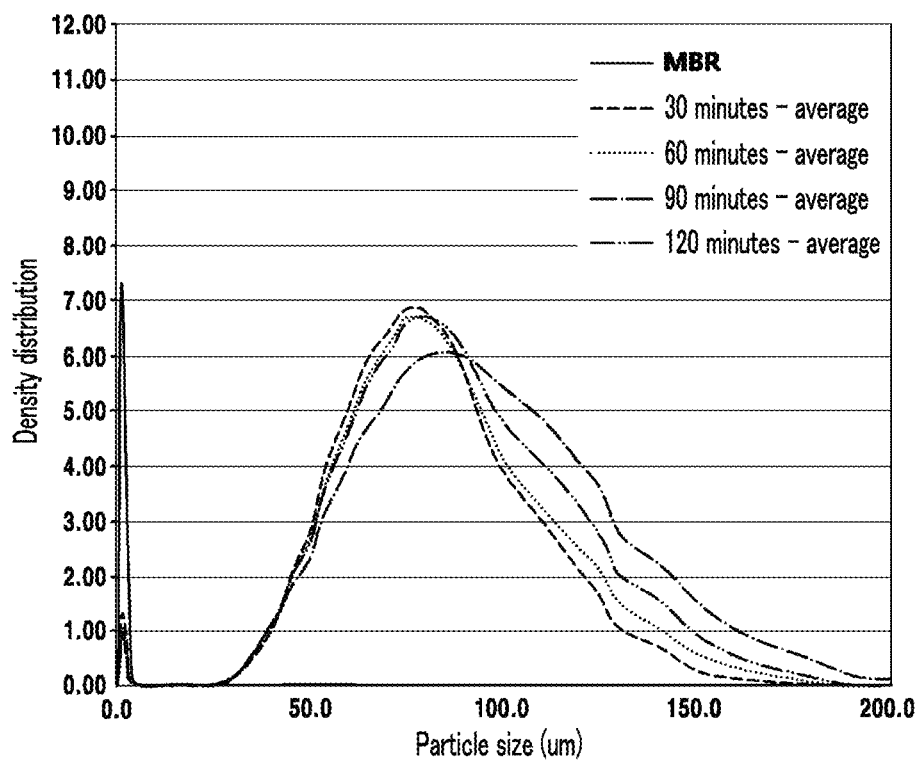
FIG. 9 shows graphs comparing the sizes of killed lactic acid bacteria prepared according to an example of the present disclosure before (FIG. 9A) and after (FIG. 9B) the killed lactic acid bacteria pass through a second membrane filter.
Figure 9B:
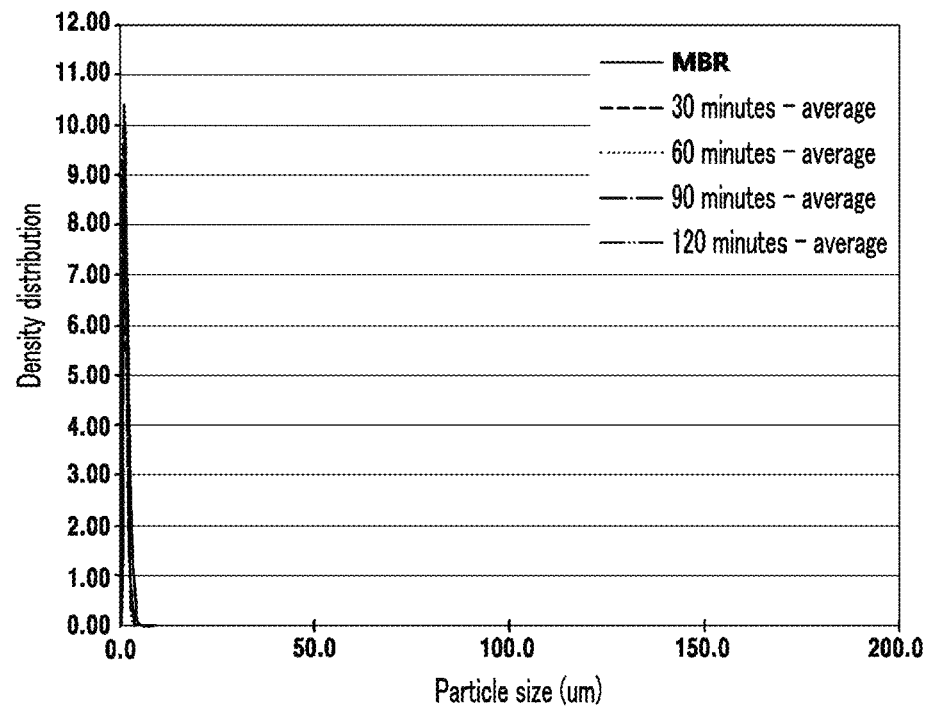
Figure 10A:
FIG. 10 shows photos comparing the properties, i.e., chromaticity, of killed lactic acid bacteria powder prepared according to an example of the present disclosure (FIG. 10A) and Comparative Example (FIG. 10B).
Figure 10B:
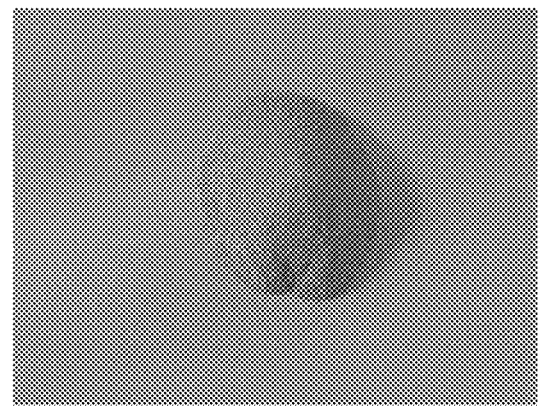

In an example of the present disclosure, the live lactic acid bacteria obtained from Example 1 were circulated at 80° C. for 0 second, 30 seconds, 60 seconds, 90 seconds, and 120 seconds, respectively, to prepare killed lactic acid bacteria (Example 2-4, FIG. 9).

Example 3. Concentration, Wash, and Dispersion of Killed Lactic Acid Bacteria Using Second Membrane Filter A medium including the killed lactic acid bacteria obtained from Example 2-1 was allowed to pass through a second membrane filter (a polysulfone hollow fiber membrane filter including pores having a diameter of from 0.01 μm to 0.1 μm and having a channel radius of 3 mm) to concentrate the killed lactic acid bacteria two to ten times. The second membrane filter was used to apply shear force to the lactic acid bacteria culture fluid including agglomerated lumps of the killed lactic acid bacteria generated during killing of the lactic acid bacteria and thus disperse the killed lactic acid bacteria.

In addition, to maximize dispersion of lactic acid bacteria by the second membrane filter, a dispersing agent was added to the medium. All the results were as shown in the following Table 2 and FIG. 8 and FIG. 9.

As shown in FIG. 8, when the killed lactic acid bacteria were concentrated and washed using the second membrane filter, the killed lactic acid bacteria agglomerated during heat treatment were collected as being dispersed and concentrated. Further, it is obvious to a person with ordinary skill in the art that even when the second membrane filter was used, impurities were filtered and removed from the culture fluid as in the first membrane filter.

As described above, lactic acid bacteria agglomerate to lumps of killed lactic acid bacteria during killing of the lactic acid bacteria. In the present example, the sizes of lumps of killed lactic acid bacteria agglomerated right after killing of lactic acid bacteria were measured in the range of from 20 μm to 200 μm (FIG. 9). The lumps of the killed lactic acid bacteria were dispersed by allowing the killed lactic acid bacteria or the lumps of the killed lactic acid bacteria obtained right after killing of the lactic acid bacteria to pass through the second membrane filter. The sizes of the dispersed killed lactic acid bacteria were measured in the range of from 0.5 μm to 3.0 μm (FIG. 9).

Example 4. Wash, Drying, and Pulverization of Killed Lactic Acid Bacteria

After concentration of the killed lactic acid bacteria according to Example 3, sterilized distilled water was added as a wash solution to the culture device and allowed to pass through the second membrane filter to wash the liquid killed lactic acid bacteria.

After the sterilized distilled water was added twice in volume of the medium including the concentrated killed lactic acid bacteria, a process of concentrating the diluted medium to a volume before being diluted was repeated three times while the sterilized distilled water passed through the second membrane filter. As a result, the concentrated killed lactic acid bacteria were washed with the sterilized distilled water of six times in volume of the medium including the concentrated killed lactic acid bacteria.

The killed lactic acid bacteria washed as described above were dried in a lyophilizer for a total of 96 hours to pulverize the killed lactic acid bacteria.

The size distributions of the killed lactic acid bacteria washed, dried, and pulverized as described above were measured as shown in FIG. 9. FIG. 9 shows that the sizes of the pulverized killed lactic acid bacteria were in the range of from 0.5 μm to 3.0 μm and 60% to 100% of the pulverized killed lactic acid bacteria had sizes of 1.0 μm or less. This is because lumps of the killed lactic acid bacteria agglomerated to sizes of from 40 μm to 200 μm during the heat treatment were dispersed by shear force applied to the culture fluid by the second membrane filter.

Comparative Example 1. Preparation of Killed Lactic Acid Bacteria Using Batch Culture Batch culture of lactic acid bacteria was conducted using a total of 80 L of a culture fluid in a 100 L-fermentor (KoBioTech). First, 4.0 L ((5.0 w/v %) of the culture fluid including live lactic acid bacteria cultured through seed culture was inoculated into the 100 L-fermentor.

During culture in a batch-type culture device, the stirring speed was 30 rpm and the temperature was maintained at 32° C. Further, anaerobic conditions were maintained using a nitrogen gas and the pH was maintained in the range of from pH 5.0 to pH 7.0 by using an ammonia gas during culture. During this batch culture, the live lactic acid bacteria were sampled at regular intervals to analyze properties thereof.

Then, in an example of the present disclosure, heat treatment was performed to the live lactic acid bacteria at 110° C. for five minutes to kill the live lactic acid bacteria (Comparative Example 1-1, FIG. 5). As shown in FIG. 5, the killed lactic acid bacteria prepared by the conventional batch culture were greater in size and less concentrated than the killed lactic acid bacteria prepared according to the present disclosure.

Then, in an example of the present disclosure, the live lactic acid bacteria were circulated three times at 120° C. C for 3 seconds to prepare killed lactic acid bacteria (Comparative Example 1-2, FIG. 7). As shown in FIG. 7, the killed lactic acid bacteria prepared by the conventional batch culture were greater in size than the killed lactic acid bacteria prepared according to the present disclosure.

In addition, the killed lactic acid bacteria were dried and pulverized in the same manner as in Example 4.

TEST EXAMPLE

Test Example 1. Evaluation of Productivity and Growth Rate of Live Lactic Acid Bacteria Table 1 compares the productivity and growth rate of the live lactic acid bacteria prepared according to Example 1 and Comparative Example 1. The productivity of the live lactic acid bacteria is represented as the amount of pellets, and the specific growth rate (m) of the live lactic acid bacteria was represented by the following Equation 4.

$$\mu = \left[ \frac{LN \frac{t_2}{t_1}}{t} \right]$$ [Equation 4]

Herein, LN represents a logarithmic function equation, t1 represents the concentration of live lactic acid bacteria at a specific time t1, t2 represents the concentration of live lactic acid bacteria at a specific time t2, and t represents elapsed time.

TABLE 1

| Culture method | Item | Unit | LM1001 | LM1004 |
|---|---|---|---|---|
| Comparative Example | Culture time | (h) | 12 | 12 |
| | Amount of pellets | (g/L) | 18.3 | 15.2 |
| | Viable cell count | (cfu/L) | 1.10E+10 | 9.30E+09 |
| | Feeding | (h$^{-1}$) | 0.0 | 0.0 |
| | Lactic acid | mM | 478.1$_{max}$ | 534.1$_{max}$ |
| | Growth rate (μl) | (h$^{-1}$) | 0.2971 | 0.2814 |
| Example | Culture time | (h) | 24 | 24 |
| | Amount of pellets | (g/L) | 205.8 | 170.0 |
| | Viable cell count | (cfu/L) | 165E+11 | 1.35E+11 |
| | Feeding | (h$^{-1}$) | 0.99 | 0.99 |
| | Lactic acid | mM | 324.3-653.7 | 369.2-675.2 |
| | Growth rate 2 | (h$^{-1}$) | 0.2117 | 0.1876 |

Herein, the feeding rate (h$^{-1}$) refers to the speed of the newly inoculated medium supplied into the culture device after the intermediate culture and before the culture and concentration of the live lactic acid bacteria through the first membrane filter in Example 1, and was analyzed according to the following Equation 5.

$$F_r = Q_h/V \quad \text{[Equation 5]}$$

Herein, $Q_h$ represents the amount (L) of the medium consumed in an hour and V represents the total volume (L) of the bioreactor.

As shown in Table 1, the live lactic acid bacteria prepared according to Comparative Example 1 contained pellets in the amounts of 18.3 g/L (LM1001) and 15.2 g/L (LM1004), whereas the live lactic acid bacteria prepared according to Example 1 contained pellets in the amounts of 205.8 g/L (LM1001) and 170.0 g/L (LM1004), which means excellent productivity.

Further, the culture fluid of the live lactic acid bacteria prepared according to Comparative Example 1 had lactic acid concentrations of 478.1 mM (LM1001) and 534.1 mM (LM1004), whereas the culture fluid of the live lactic acid bacteria prepared according to Example 1 had lactic acid concentrations of 324.3 mM (LM1001) and 369.2 mM (LM1004).

Thus, it can be seen that according to the preparation method of Example 1, impurities such as lactic acid and the like were continuously filtered and removed through the first membrane filter at a constant concentration during culture. Therefore, it can be seen that the impurities were maintained at a constant concentration, and, thus, the final amount of lactic acid bacteria increased, compared to Comparative Example 1.

Test Example 2. Evaluation of Regulation of Sizes of Live Lactic Acid Bacteria

The live lactic acid bacteria prepared according to Example 1 and Comparative Example 1 were collected and dried and pulverized. Then, images of live lactic acid bacteria present in the powder were taken with a scanning electron microscope (SEM, ×10,000) as shown in FIG. 4 and with an optical microscope (×1,000) as shown in FIG. 5.

Figure 6:
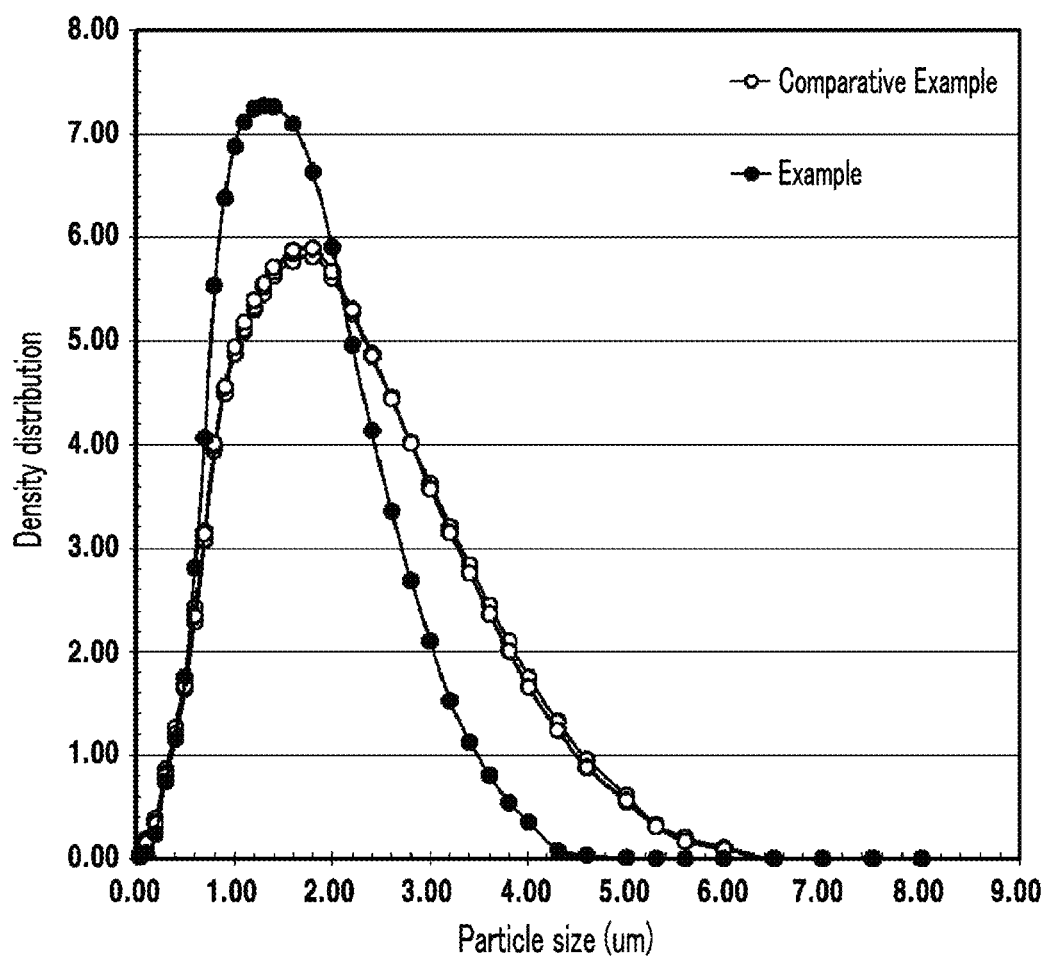
FIG. 6 is a graph comparing size distributions of live lactic acid bacteria cultured and concentrated according to an example of the present disclosure and live lactic acid bacteria cultured according to Comparative Example 1.

Further, the size distributions of the live lactic acid bacteria prepared according to Example 1 and Comparative Example 1 were measured as shown in FIG. 6.

Figure 4A:
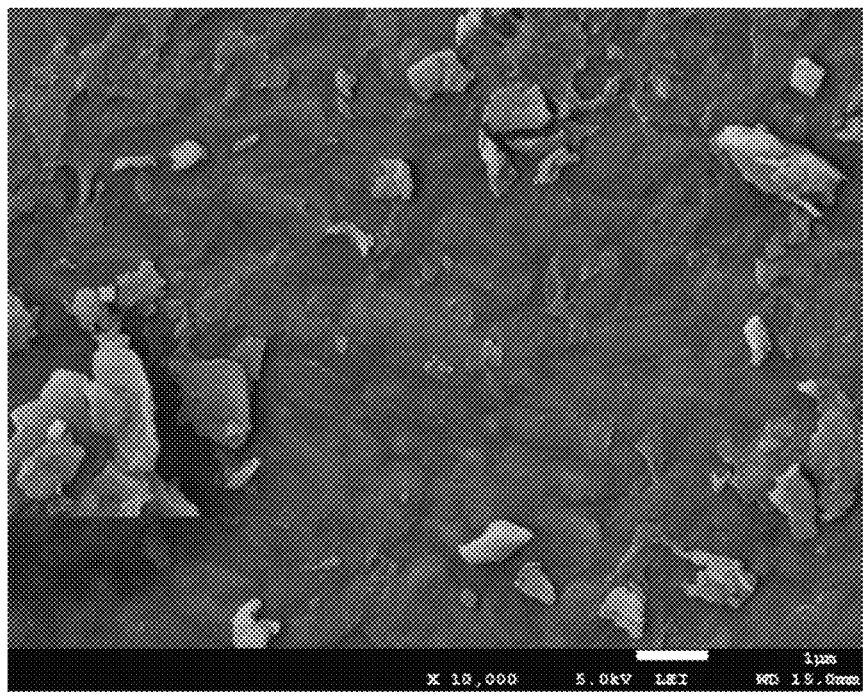
FIG. 4 shows scanning electron microscope (SEM) images (×10,000) comparing killed lactic acid bacteria lyophilized according to an example of the present disclosure (FIG. 4A) and killed lactic acid bacteria prepared according to Comparative Example 1 (FIG. 4B).
Figure 4B:
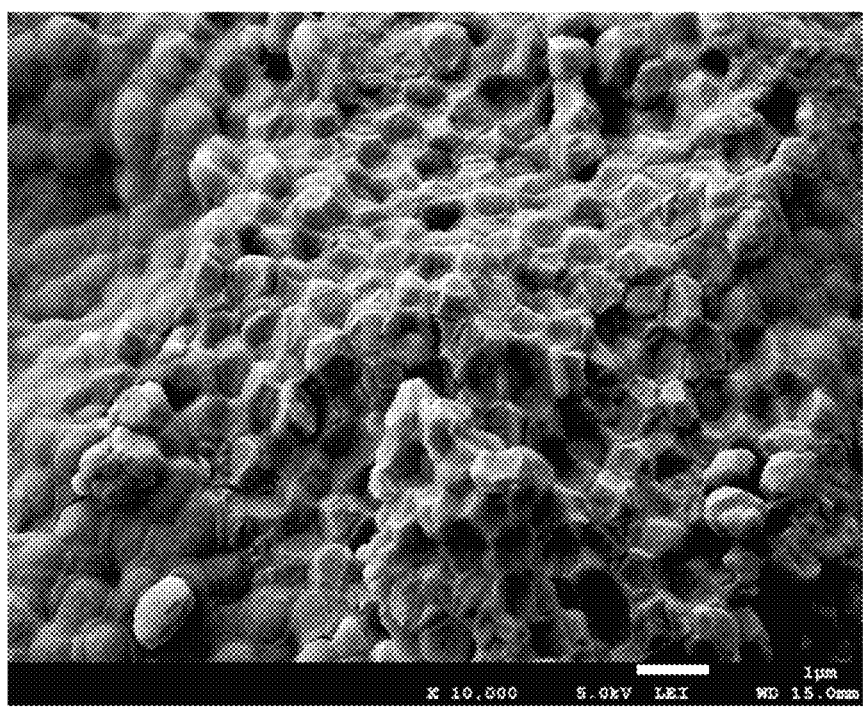

As shown in FIG. 4 and FIG. 5, the live lactic acid bacteria prepared according to Example 1 were smaller in size and more concentrated than the live lactic acid bacteria prepared according to Comparative Example 1.

Furthermore, as shown in FIG. 6, the live lactic acid bacteria prepared according to Comparative Example 1 had a size distribution of up to 6.3 μm, whereas the live lactic acid bacteria prepared according to Example 1 had a smaller size distribution of up to 4.0 μm. Moreover, when the live lactic acid bacteria prepared according to Example 1 were killed by heat treatment, the sizes thereof decreased to 3.0 μm, which is remarkably smaller than 4.0 μm of Comparative Example 1.

Test Example 3. Evaluation of Regulation of Sizes of Killed Lactic Acid Bacteria Table 2 compares properties when using the second membrane filter according to Example 3 and properties when using centrifugation according to Comparative Example during collection of the killed lactic acid bacteria according to Example 2-1.

TABLE 2

| | Classification | Comparative Example (Centrifugation) | Example 1 (Group 1) | Example 2 (Group 2) | Example 3 (Group 3) |
|---|---|---|---|---|---|
| Fermented broth | Liquid measure (L) | 10 | 10 | 10 | 10 |
| | Total cell density (No/ml) | 1.10E+11 | 1.78E+11 | 1.78+11 | 1.62E+22 |
| | Total cell count (No) | 1.10E+15 | 1.78E+15 | 1.78E+15 | 1.62E+15 |
| | Cumulative yield (%) | 100 | 100 | 100 | 100 |
| Heat treatment (Sterilization) | Liquid measure (L) | 10 | 10 | 10 | 10 |
| | Total cell density (No/ml) | 4.71E+10 | 7.62E+10 | 1.52E+11 | 1.38E+11 |
| | Total cell count (No | 4.71E+14 | 7.62E+14 | 1.52E+15 | 1.38E+15 |
| | Cumulative yield (%) | 42.8 | 42.8 | 85.4 | 85.2 |
| Concentration/ Wash | Liquid measure (L) | 2 | 2 | 2 | 2 |
| | Total cell density (No/ml) | 1.45E+11 | 1.03E+12 | 1.32E+12 | 1.37E+12 |
| | Total cell count (No | 2.90E+14 | 2.05E+15 | 2.64E+15 | 2.73E+15 |
| | Cumulative yield (%) | 26.4 | 115.2 | 148.5 | 168.7 |
| Dry (F/d) | Liquid measure (L) | 0.478 | 0.543 | 0.498 | 0.505 |
| | Total cell density (No/ml) | 4.19E+11 | 3.70E+12 | 5.19E+12 | 5.23E+12 |
| | Total cell count (No | 2.00E+14 | 2.01E+15 | 2.58E+15 | 2.64E+15 |
| | Cumulative yield (%) | 18.2 | 112.8 | 145.1 | 162.9 |

As shown in Table 2, the cumulative yield increased to 115.2% (Group 1), 148.5% (Group 2), and 168.7% (Group 3) according to Example 3. However, when the killed lactic acid bacteria were collected by centrifugation according to Comparative Example, agglomeration of the killed lactic acid bacteria occurred more severely and the cumulative yield decreased sharply to 26.4%.

Test Example 4. Evaluation of Suspension Properties of Killed Lactic Acid Bacteria The present test was conducted to examine the aqueous suspension stability of the killed lactic acid bacteria powder prepared according to Example 4 and Comparative Example 1-1.

In the test, *Lactobacillus plantarum* (LM1001) was used to prepare 1.0E+12/g of killed lactic acid bacteria powder according to Example 4 and Comparative Example 1-1. Then, the killed lactic acid bacteria powder of Example 4 and the killed lactic acid bacteria powder of Comparative Example 1-1 were suspended in sterilized distilled water at a concentration of 1.0E+8/ml and 1.0E+7/ml, respectively, to examine deposition thereof at room temperature for 4 days (FIG. 11).

The total cell density of the killed lactic acid bacteria powder prepared by the culture of the preparation method of the present disclosure was 5.2E+12/g and the total cell density of the killed lactic acid bacteria powder prepared by the batch culture was 2.9E+12/g.

Figure 11B:
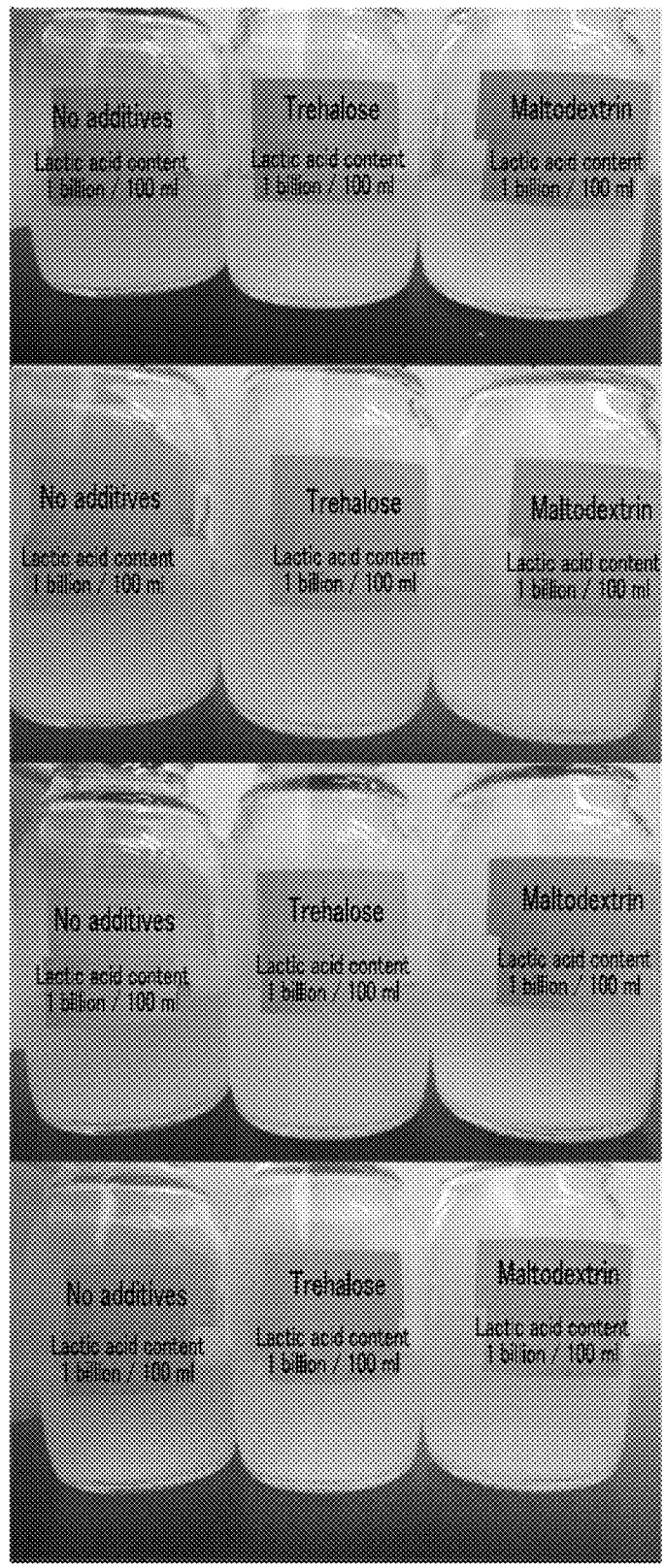
FIG. 11 compares the results of the suspension of killed lactic acid bacteria powder prepared according to an example of the present disclosure (FIG. 11B and FIG. 11D) and Comparative Example (FIG. 11A and FIG. 11C) in distilled water.
FIG. 11A show the results of 1 day [FIG. 11A(i)], 2 days [FIG. 11A(ii)], 3 days [FIG. 11A(iii)], and 4 days [FIG. 11A(iv)] after the suspension of killed lactic acid bacteria powder (1 billion/100 ml) prepared according to Comparative Example, FIG. 11B show the results of 1 day [FIG. 11B(i)], 2 days [FIG. 11B(ii)], 3 days [FIG. 11B(iii)], and 4 days [FIG. 11B(iv)] after the suspension of killed lactic acid bacteria powder (1 billion/100 ml) prepared according to an example of the present disclosure, FIG. 11C show the results of 1 day [FIG. 11C(i)], 2 days [FIG. 11C(ii)], 3 days [FIG. 11C(iii)], and 4 days [FIG. 11C(iv)] after the suspension of killed lactic acid bacteria powder (10 billion/100 ml) prepared according to Comparative Example and FIG. 11D show the results of 1 day [FIG. 11D(i)], 2 days [FIG. 11D(ii)], 3 days [FIG. 11D(iii)], and 4 days [FIG. 11D(iv)] after the suspension of killed lactic acid bacteria powder (10 billion/100 ml) prepared according to an example of the present disclosure.
Figure 11C:
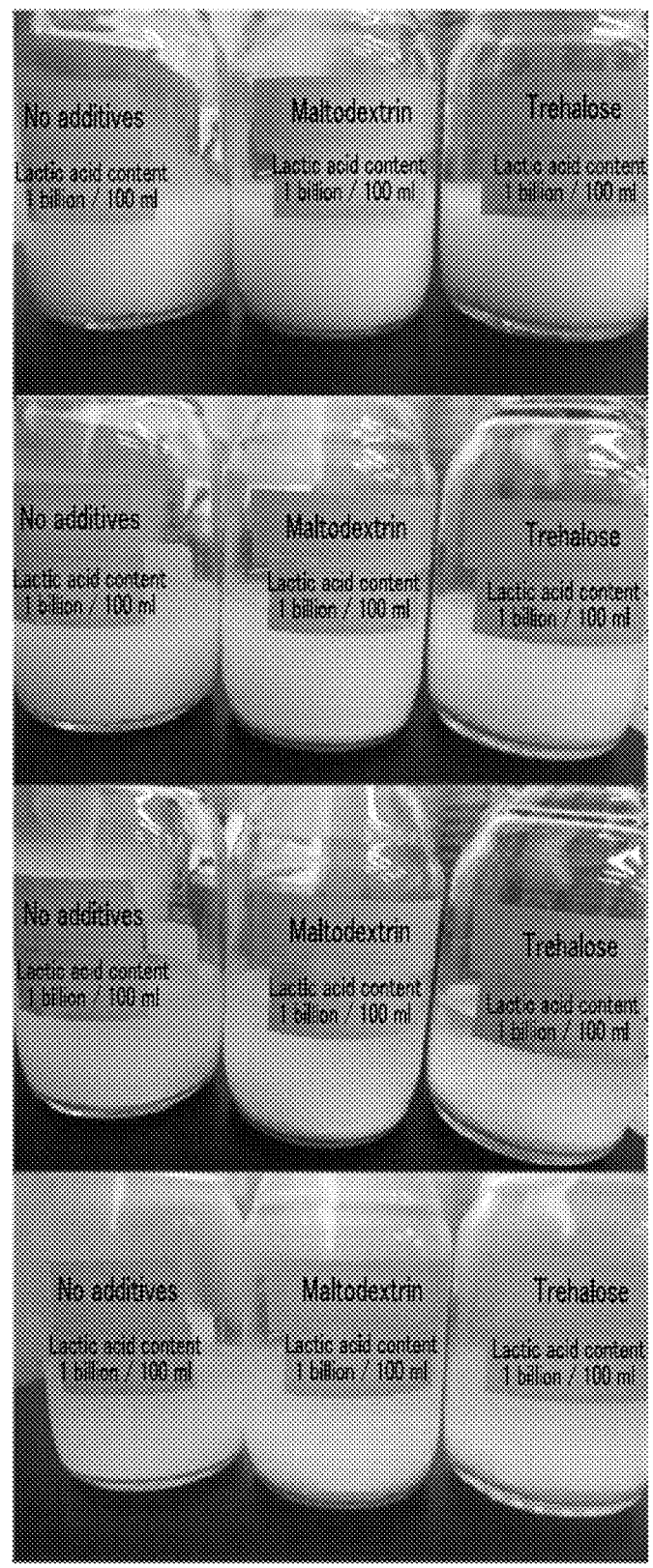

As shown in FIG. 11, some deposits occurred in an hour of suspension according to the batch culture, whereas the suspension was maintained stably for four days after suspension according to the preparation method of the present disclosure.

Test Example 5. Analysis of Immune Activity of Live Lactic Acid Bacteria

The immune activities of two kinds of live and killed lactic acid bacteria of *L. plantarum* prepared by the preparation method of the present disclosure were analyzed.

Figure 12A:
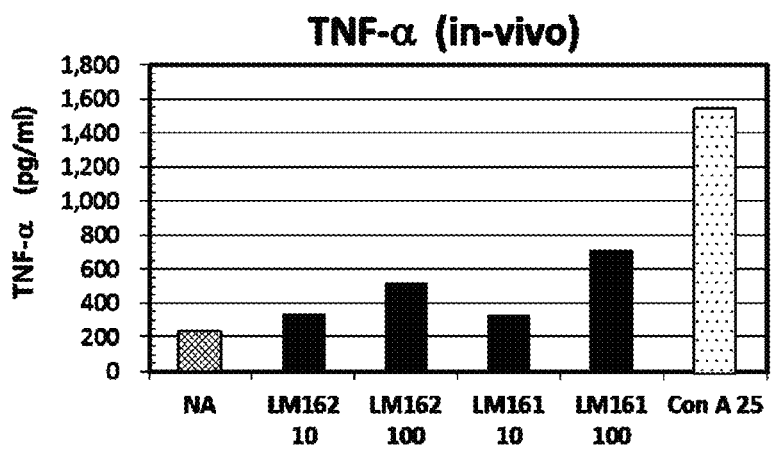
FIG. 12 provides graphs showing the immune activity of live lactic acid bacteria according to an example of the present disclosure and shows the results of measurement of the amounts of TNF-α (FIG. 12A), INF-γ (FIG. 12B) and IL-12 (FIG. 12C) produced in mouse bloods.
Figure 12B:
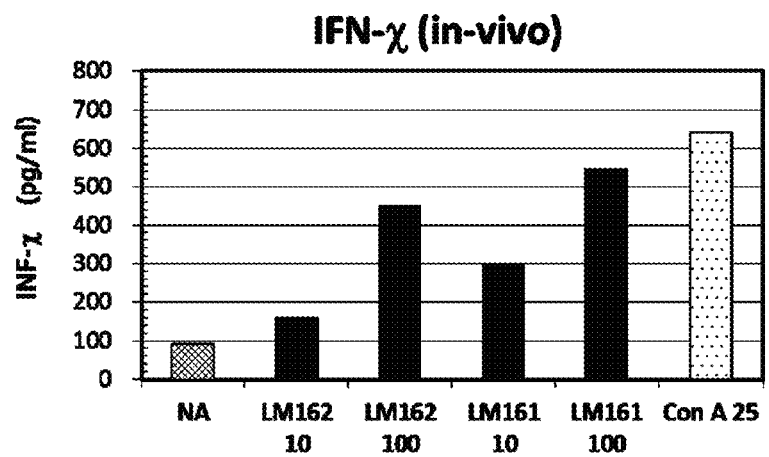
Figure 12C:
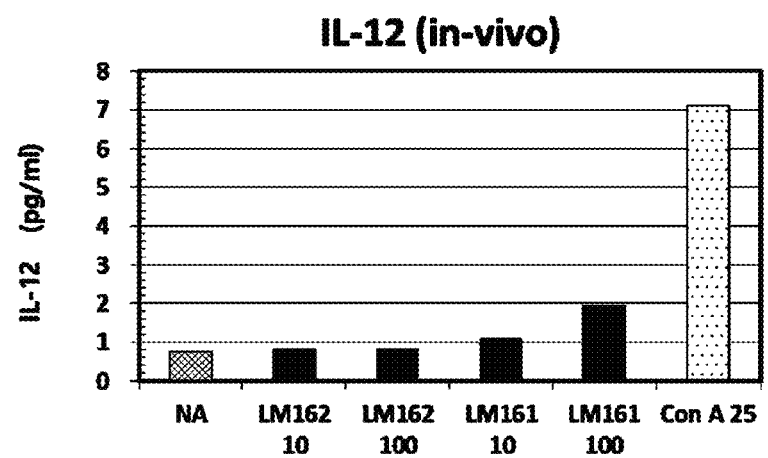

The immune activities of the live lactic acid bacteria were analyzed through an in-vivo test in which a feed including the live lactic acid bacteria was fed to mice and then and changes in concentration of cytokines TNF-α, INF-γ, IL-12 in blood of the mice were measured as shown in FIG. 12.

Specifically, two kinds of live lactic acid bacteria were orally administered to 6-week-old male Balb/c mice for respective concentrations (10 mg/kg, 100 mg/kg) once a day for 10 days. Blood samples were obtained from the test animals 24 hours after the last oral administration and kept at −80° C. and used for the test. A positive control was administered intravenously with 25 mg/kg of Con A.

As shown in FIG. 12, after treatment with the lactic acid bacteria for 10 days, the amounts of serum cytokines were measured by ELISA assay. All the cytokines TNF-α, IFN-γ, and IL-12 were increased significantly, compared to the positive control Con A (25 mg/kg).

Test Example 6. Analysis of Immune Activity of Killed Lactic Acid Bacteria

The immune activities of two kinds of killed lactic acid bacteria of *L. plantarum* prepared by the preparation method of the present disclosure were analyzed.

The immune activities of the killed lactic acid bacteria were analyzed through an in-vitro test in which a cytotoxicity test was conducted using macrophages RAW 264.7 and the amount of NO (nitric oxide) and the amounts of cytokines TNF-α, INF-γ, IL-12, and IL-6 caused by mouse splenocytes were measured.

According to the above-described processes of the analysis method, the cytotoxicity of the killed lactic acid bacteria and the function of inducing the production of nitric oxide were examined using the macrophages RAW 264.7.

Figure 13A:
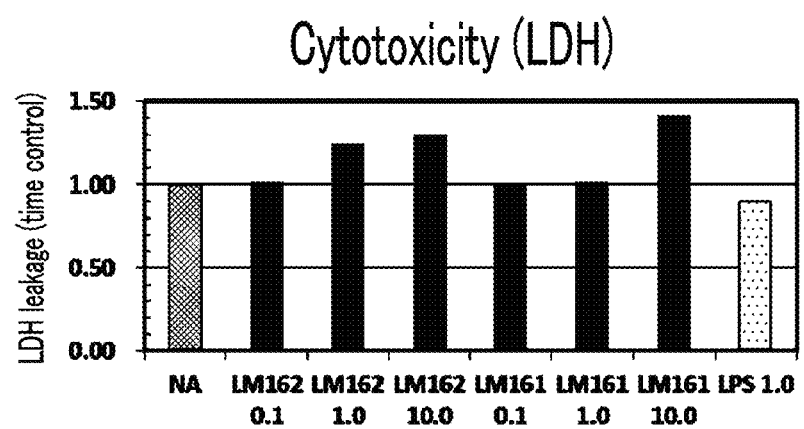
FIG. 13 provides graphs showing the immune activity of killed lactic acid bacteria according to an example of the present disclosure and shows the results of measurement of the cytotoxicity (LDH, FIG. 13A) and the amount of nitric oxide (FIG. 13B) produced in the macrophage cell strain RAW264.7.

FIG. 13A shows the result of a cytotoxicity test with lactic acid bacteria samples treated for 48 hours to set a cell treatment concentration of lactic acid bacteria in mouse macrophages RAW 264.7 and shows that the cytotoxicity was not detected at a concentration of 10 μg/ml or less. Therefore, the immune activities of the lactic acid bacteria samples were measured in a concentration range (from 0.1 μg/ml to 10 μg/ml) in which the cytotoxicity was not detected. The cytotoxicity was measured as the activity of free dactate dehydrogenase.

Figure 13B:
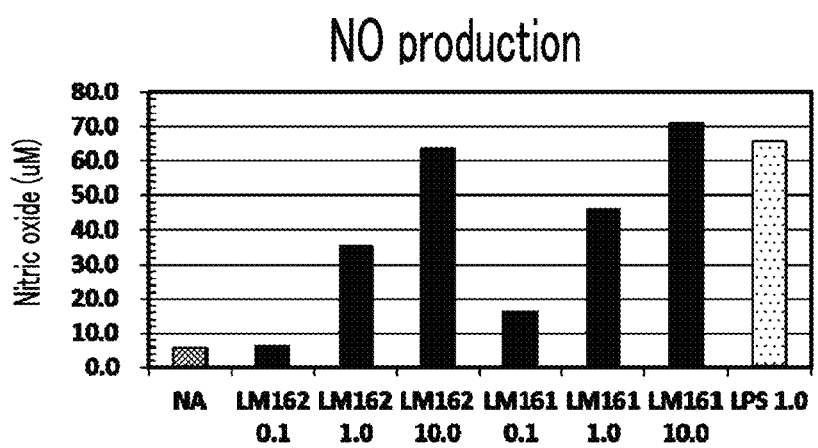
Figure 14A:
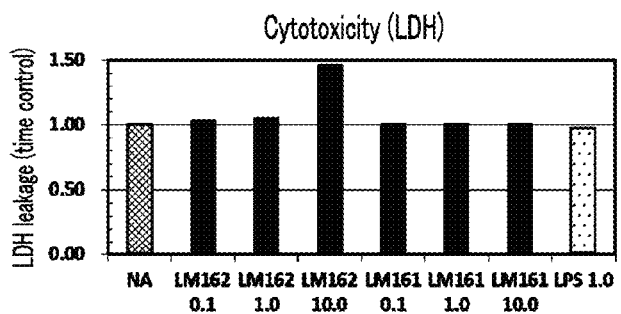
FIG. 14 provides graphs showing the immune activity of killed lactic acid bacteria according to an example of the present disclosure and shows the results of measurement of the cytotoxicity (LDH, FIG. 14A) and the amounts of TNF-α (FIG. 14B), INF-γ (FIG. 14C), IL-12 (FIG. 14D) and IL-6 (FIG. 14E) produced in mouse splenocytes.
Figure 14B:
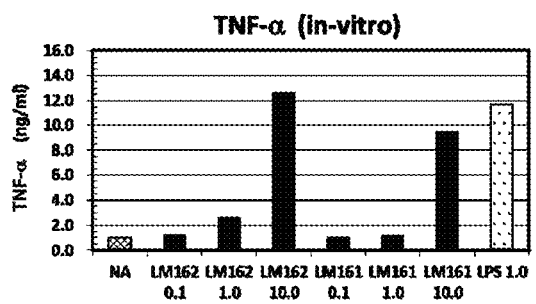
Figure 14C:
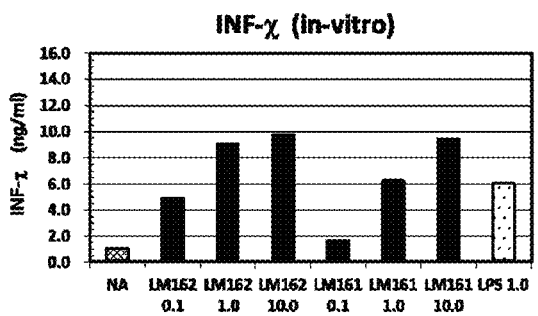
Figure 14D:
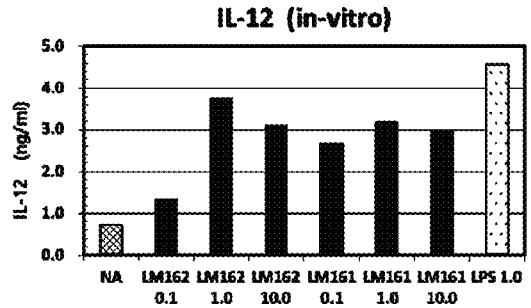
Figure 14E:
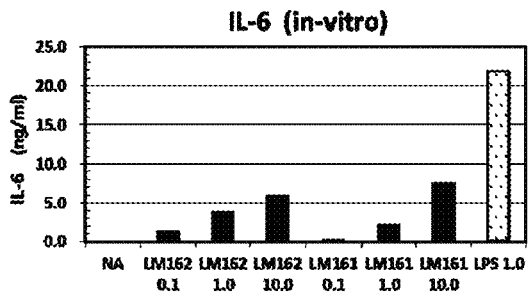

FIG. 13B shows the result of measuring the activity of NO isolated in a culture medium with a Griess reagent system after mouse macrophages RAW 264.7 were treated with lactic acid bacteria samples at a concentration of 0.1 μg/ml, 1 μg/ml, 10 μg/ml, respectively, for 48 hours to evaluate the effect of killed lactic acid bacteria powder on the production of NO from the mouse macrophages RAW 264.7.

As shown in FIG. 13, the NO productivity increased about six times by the positive control LPS and significantly increased in a concentration-dependent manner in all of the treated lactic acid bacteria samples.

FIG. 14 shows the effect of killed lactic acid bacteria powder on the production of cytokines using mouse splenocytes. FIG. 14A shows that the cytotoxicity was not detected under a treatment concentration of 0.1 mg/ml to 10 mg/ml of the killed lactic acid bacteria powder. Further, FIG. 14B, FIG. 14C, FIG. 14D, and FIG. 14E show that the treatment with the killed lactic acid bacteria powder significantly increased the production of cytokines in a concentration-dependent manner.

As shown in FIG. 12 to FIG. 14, both the two kinds of live and killed lactic acid bacteria exhibit immunopotentiating properties and immune activities.

Test Example 7. Anti-Obesity Effect of Killed Lactic Acid Bacteria

Figure 15A:
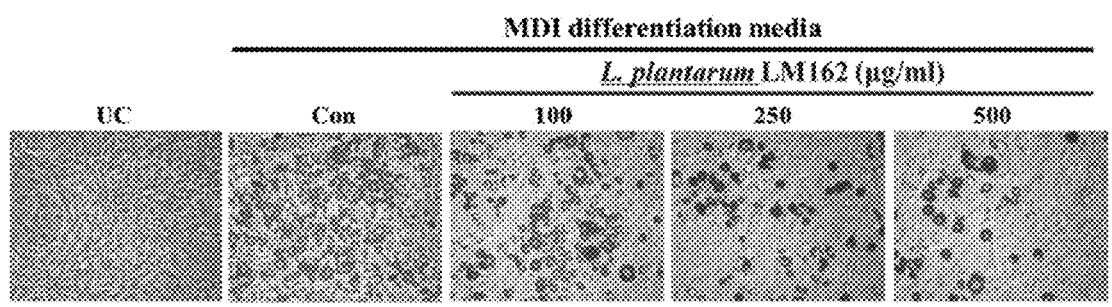
FIG. 15 provides photos (FIG. 15A) and graphs (FIG. 15B to FIG. 15D) showing the anti-obesity effect of killed lactic acid bacteria according to an embodiment of the present disclosure and shows that lipid accumulation in tested adipocytes decreases in inverse proportion to an increase in concentration of treated killed lactic acid bacteria.
FIG. 15B to FIG. 15D shows the viability (FIG. 15B) and the results of measurement of the amounts of lipid in adipocytes by Oil Red-O staining analysis (FIG. 15C) and triglycerides in adipocytes (FIG. 15D).
Figure 15B:
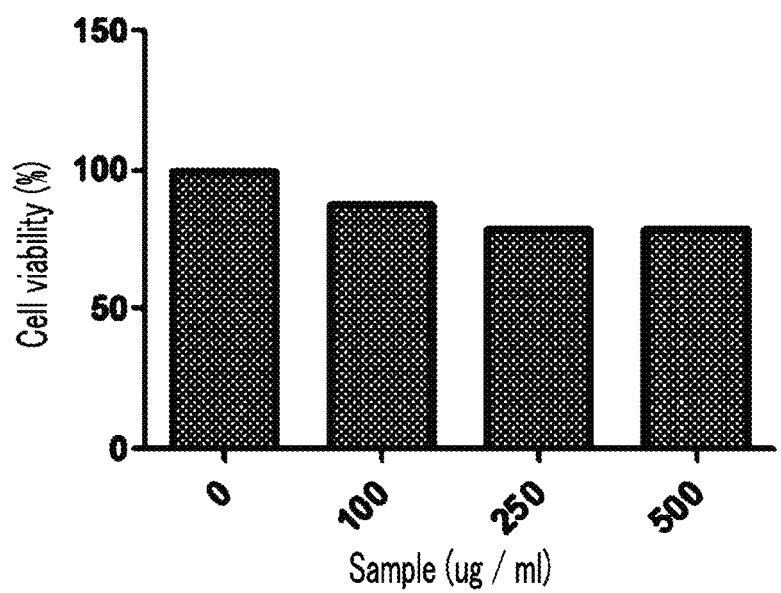

A test for suppressing lipid accumulation in adipocytes was conducted to examine the anti-obesity effect of killed lactic acid bacteria. Specifically, 25 mg/ml of Con A which is an inducer of lipid accumulation was added to adipocytes and the adipocytes were treated with killed lactic acid bacteria powder of *L. planatrum* (LM1004) for respective concentrations (0 μg/ml, 100 μg/ml, 250 μg/ml, and 500 μg/ml) and the amounts of decreased liquid accumulation were measured. As control groups, a group which was not treated with the inducer of lipid accumulation and a group which was treated with the inducer of lipid accumulation but not treated with the killed lactic acid bacteria powder were used. As shown in FIG. 15, a concentration-dependent decrease in amount of lipid accumulation in adipocytes depending on the treatment concentration (0 μg/ml, 100 μg/ml, 250 μg/ml, and 500 μg/ml) of the killed lactic acid bacteria powder was observed with a microscope (FIG. 15A).

Figure 15C:
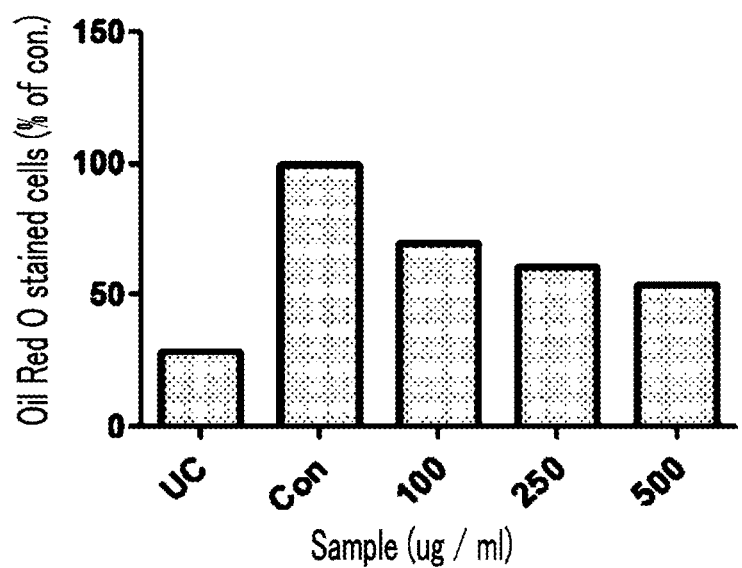

Particularly, at a concentration of 500 μg/ml, a decrease of lipid in adipocytes by about 46% compared to the positive control Con A was confirmed by Oil Red-O staining analysis (FIG. 15C).

Figure 15D:
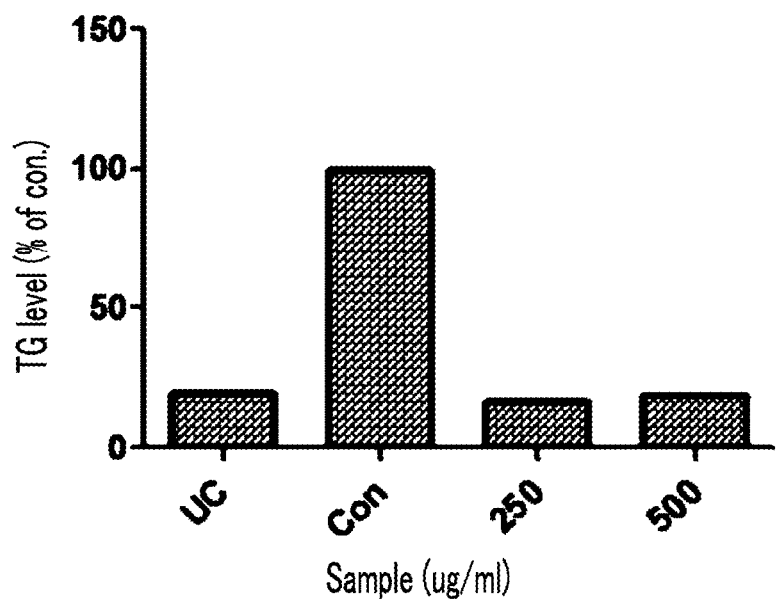

Also, a decrease in amount of triglycerides accumulated in adipocytes depending on the treatment concentration (0 µg/ml, 250 µg/ml, and 500 µg/ml) was observed. Particularly, at a concentration of 500 µg/ml, a decrease of triglycerides (TG) in adipocytes by about 81% compared to the positive control Con A was observed (FIG. 15D).

Test Example 7 Confirmed that LM1004 can Even Suppress Lipid Accumulation in Adipocytes The above description of the present disclosure is provided for the purpose of illustration, and it would be understood by a person with ordinary skill in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

ACCESSION NUMBER

Name of Depository Institution: Korean Culture Center of Microorganisms (Overseas)
Accession Number: KCCM 43246
Date of Deposit: Oct. 28, 2016
Name of Depository Institution: Korean Culture Center of Microorganisms
Accession Number: KCCM 42959
Date of Deposit: Nov. 12, 2010

We claim:

1. A method for preparing killed lactic acid bacteria using a bioreactor including a culture device and a membrane filter, the membrane filter including a first membrane filter and a second membrane filter and the bioreactor having a structure in which a fluid added to the culture device independently passes through the first membrane filter and the second membrane filter and then is delivered again to the culture device, the method comprising:
   adding a medium inoculated with live lactic acid bacteria into the culture device;
   culturing and concentrating the live lactic acid bacteria by allowing the medium inoculated with the live lactic acid bacteria to pass through the first membrane filter, comprising:
      reducing sizes of the live lactic acid bacteria by a shear force applied to the medium by the first membrane filter, and
      controlling the shear force by controlling a flow rate of the lactic acid bacteria medium passing through the first membrane filter;
   killing the cultured and concentrated live lactic acid bacteria to prepare killed lactic acid bacteria;
   concentrating the killed lactic acid bacteria by allowing the medium including the killed lactic acid bacteria to pass through the second membrane filter; and
   drying and pulverizing the concentrated killed lactic acid bacteria.

2. The method for preparing killed lactic acid bacteria of claim 1, wherein the live lactic acid bacteria inoculated into the medium are cultured through one or more culture phases.

3. The method for preparing killed lactic acid bacteria of claim 1,
   wherein the bioreactor further includes a tank for preparing a medium and a membrane filter for preparing a medium, and
   the bioreactor has a structure, in which a culture medium solution added into the tank for preparing a medium passes through the membrane filter for preparing a medium and is delivered again to the tank for preparing a medium or delivered to the culture device, and
   the medium is prepared by allowing the culture medium solution to pass through the membrane filter for preparing a medium, and
   the culture medium solution is sterilized by filtering impurities included in the culture medium solution through the membrane filter for preparing a medium.

4. The method for preparing killed lactic acid bacteria of claim 3, wherein the membrane filter for preparing a medium includes a hollow fiber membrane filter including pores having a diameter of from 0.1 µm to 1.0 µm.

5. The method for preparing killed lactic acid bacteria of claim 1, wherein the live lactic acid bacteria are concentrated by filtering the impurities included in the medium inoculated with the live lactic acid bacteria through the membrane filter.

6. The method for preparing killed lactic acid bacteria of claim 1, wherein the pH of the medium inoculated with the live lactic acid bacteria is maintained in the range of from pH 5.0 to pH 7.0 during the culture and concentration of the live lactic acid bacteria.

7. The method for preparing killed lactic acid bacteria of claim 1, wherein the killing includes a treatment at 80° C. to 121° C. for 3 minutes to 15 minutes.

8. The method for preparing killed lactic acid bacteria of claim 1, wherein
   the killing includes 1 to 10 times of ultra-high temperature sterilization, and
   the ultra-high temperature sterilization includes a treatment at 110° C. to 130° C. for 3.0 seconds to 10.0 seconds.

9. The method for preparing killed lactic acid bacteria of claim 1, wherein the killed lactic acid bacteria are concentrated, dispersed, and washed by passing through the second membrane filter.

10. The method for preparing killed lactic acid bacteria of claim 1, wherein
    the first membrane filter includes a hollow fiber membrane filter including pores having a diameter of from 0.1 µm to 1 µm, and
    the second membrane filter includes a hollow fiber membrane filter including pores having a diameter of from 0.01 µm to 0.1 µm.

11. The method for preparing killed lactic acid bacteria of claim 1, wherein the second membrane filter includes a hollow fiber membrane filter capable of filtering a material having a molecular weight of from 50,000 daltons to 100,000 daltons.

12. The method for preparing killed lactic acid bacteria of claim 1, further comprising:
    after the culturing and concentrating of the live lactic acid bacteria, adding a dispersing agent into the medium inoculated with the live lactic acid bacteria.

13. The method for preparing killed lactic acid bacteria of claim 12, wherein the dispersing agent is added in the amount of 0.1% (w/w) to 80.0% (w/w) with respect to pellets of the cultured and concentrated live lactic acid bacteria.

14. The method for preparing killed lactic acid bacteria of claim 1, wherein sizes of the pulverized killed lactic acid bacteria are in the range of 0.01 μm to 3.0 μm.

15. The method for preparing killed lactic acid bacteria of claim 1, wherein 40% to 100% of the pulverized killed lactic acid bacteria have sizes of 1.0 μm or less.

16. The method for preparing killed lactic acid bacteria of claim 1, wherein the lactic acid bacteria include a member selected from the group consisting of a *Bacillus*, a *Coccus*, a *Bifidobacterium*, and combinations thereof.

17. The method for preparing killed lactic acid bacteria of claim 1, wherein the lactic acid bacteria include *Lactobacillus plantarum*.

18. The method for preparing killed lactic acid bacteria of claim 1, wherein the culturing and concentrating of the live lactic acid bacteria further comprises:

controlling the shear force by controlling an internal channel size of a hollow fiber membrane of the first membrane filter.

\* \* \* \* \*